United States Patent
Falkel

(10) Patent No.: US 10,925,698 B2
(45) Date of Patent: *Feb. 23, 2021

(54) DIGITAL DENTAL EXAMINATION AND DOCUMENTATION

(71) Applicant: uLab Systems, Inc., Redwood City, CA (US)

(72) Inventor: Michael I. Falkel, Carmel, CA (US)

(73) Assignee: uLab Systems, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,055

(22) Filed: Feb. 5, 2020

(65) Prior Publication Data

US 2020/0170762 A1 Jun. 4, 2020

Related U.S. Application Data

(63) Continuation of application No. 16/435,028, filed on Jun. 7, 2019, now Pat. No. 10,588,723, which is a
(Continued)

(51) Int. Cl.
*G16H 50/20* (2018.01)
*A61C 9/00* (2006.01)
(Continued)

(52) U.S. Cl.
CPC .............. *A61C 9/0046* (2013.01); *A61B 1/24* (2013.01); *A61B 5/0088* (2013.01); *G16H 10/60* (2018.01);
(Continued)

(58) Field of Classification Search
CPC ...... G06K 9/46; G06K 9/4604; G06K 9/6201; G06K 9/6202; G06T 7/0012;
(Continued)

(56) References Cited

U.S. PATENT DOCUMENTS

| 4,068,379 A | 1/1978 | Miller et al. ................... 32/14 A |
| 4,889,485 A | 12/1989 | Iida .................................. 433/9 |

(Continued)

FOREIGN PATENT DOCUMENTS

| CA | 2557573 C | 7/2012 | ............. G06F 19/00 |
| CN | 1973291 B | 9/2010 | ............. G06F 19/00 |

(Continued)

*Primary Examiner* — Andrew W Johns
(74) *Attorney, Agent, or Firm* — Levine Bagade Han LLP

(57) ABSTRACT

Systems and methods are disclosed for processing and storing acquired data relating to one or more dental conditions. The methods can include acquiring a first oral feature in a first data acquisition using a data acquisition device, determining a first oral feature first reference point from the first data acquisition, diagnosing a first dental condition upon confirming that the first oral feature first reference point is associated with the first dental condition, acquiring the first oral feature in a second data acquisition using the data acquisition device, determining a first oral feature second reference point from the second data acquisition, and tracking the progression of the first dental condition by determining a discrepancy between the first oral feature first and second reference points.

20 Claims, 9 Drawing Sheets

Related U.S. Application Data continuation of application No. 15/710,469, filed on Sep. 20, 2017, now Pat. No. 10,357,342.

(60) Provisional application No. 62/397,504, filed on Sep. 21, 2016, provisional application No. 62/397,525, filed on Sep. 21, 2016.

(51) Int. Cl.

| | | |
|---|---|---|
| *A61B 1/24* | (2006.01) | |
| *G16H 10/60* | (2018.01) | |
| *A61B 5/00* | (2006.01) | |
| *G16H 30/40* | (2018.01) | |
| *A61B 6/14* | (2006.01) | |
| *A61B 6/00* | (2006.01) | |
| *A61B 6/03* | (2006.01) | |
| *A61C 19/04* | (2006.01) | |
| *A61B 1/00* | (2006.01) | |
| *G16H 30/20* | (2018.01) | |

(52) U.S. Cl.
CPC ............ *G16H 30/40* (2018.01); *G16H 50/20* (2018.01); *A61B 1/0005* (2013.01); *A61B 1/00009* (2013.01); *A61B 6/032* (2013.01); *A61B 6/14* (2013.01); *A61B 6/4085* (2013.01); *A61C 9/004* (2013.01); *A61C 19/04* (2013.01); *G16H 30/20* (2018.01)

(58) Field of Classification Search
CPC ................. G06T 7/0014; G06T 7/0016; G06T 2207/30036; G06F 19/321; G16H 30/00; G16H 50/20; A61C 9/004; A61C 9/0046; A61C 9/0053; A61B 6/14
See application file for complete search history.

(56) References Cited

U.S. PATENT DOCUMENTS

| | | | |
|---|---|---|---|
| 4,983,334 A | 1/1991 | Adell | 246/16 |
| 5,055,039 A | 10/1991 | Abbatte et al. | 433/24 |
| 5,186,623 A | 2/1993 | Breads et al. | 433/6 |
| 5,259,762 A | 11/1993 | Farrell | 433/215 |
| 5,691,905 A | 11/1997 | Dehoff et al. | 364/468.04 |
| 5,975,893 A | 11/1999 | Chishti et al. | 433/6 |
| 6,183,248 B1 | 2/2001 | Chishti et al. | 433/6 |
| 6,210,162 B1 | 4/2001 | Chishti et al. | 433/213 |
| 6,217,325 B1 | 4/2001 | Chishti et al. | 433/24 |
| 6,227,850 B1 | 5/2001 | Chishti et al. | 433/24 |
| 6,227,851 B1 | 5/2001 | Chishti et al. | 433/24 |
| 6,250,918 B1 | 6/2001 | Sachdeva et al. | 433/24 |
| 6,299,440 B1 | 10/2001 | Phan et al. | 433/24 |
| 6,315,553 B1 | 11/2001 | Sachdeva et al. | 433/24 |
| 6,386,878 B1 | 5/2002 | Pavlovskaia et al. | 433/215 |
| 6,390,812 B1 | 5/2002 | Chishti et al. | 433/6 |
| 6,394,801 B2 | 5/2002 | Chishti et al. | 433/24 |
| 6,398,548 B1 | 6/2002 | Muhammad et al. | 433/24 |
| 6,454,565 B2 | 9/2002 | Phan et al. | 433/6 |
| 6,463,344 B1 | 10/2002 | Pavloskaia | 700/98 |
| 6,471,511 B1 | 10/2002 | Chishti et al. | 433/24 |
| 6,485,298 B2 | 11/2002 | Chishti et al. | 433/24 |
| 6,488,499 B1 | 12/2002 | Miller | 433/24 |
| 6,524,101 B1 | 2/2003 | Phan et al. | 433/6 |
| 6,554,611 B2 | 4/2003 | Chishti et al. | 433/6 |
| 6,572,372 B1 | 6/2003 | Phan et al. | 433/6 |
| 6,582,227 B2 | 6/2003 | Phan et al. | 433/6 |
| 6,602,070 B2 | 8/2003 | Miller et al. | 433/24 |
| 6,607,382 B1 | 8/2003 | Kuo et al. | 433/6 |
| 6,626,666 B2 | 9/2003 | Chishti et al. | 433/24 |
| 6,629,840 B2 | 10/2003 | Chishti et al. | 433/24 |
| 6,682,346 B2 | 1/2004 | Chishti et al. | 433/24 |
| 6,688,885 B1 | 2/2004 | Sachdeva et al. | 433/24 |
| 6,699,037 B2 | 3/2004 | Chishti et al. | 433/24 |
| 6,702,575 B2 | 3/2004 | Hilliard | 433/6 |
| 6,705,861 B2 | 3/2004 | Chishti et al. | 433/24 |
| 6,705,863 B2 | 3/2004 | Phan et al. | 433/24 |
| 6,722,880 B2 | 4/2004 | Chishti et al. | 433/24 |
| 6,729,876 B2 | 5/2004 | Chishti et al. | 433/24 |
| 6,761,560 B2 | 7/2004 | Miller | 433/24 |
| 6,783,360 B2 | 8/2004 | Chishti | 433/6 |
| 6,786,721 B2 | 9/2004 | Chishti et al. | 433/24 |
| 6,802,713 B1 | 10/2004 | Chishti et al. | 433/24 |
| 6,830,450 B2 | 12/2004 | Knopp et al. | 433/6 |
| 6,846,179 B2 | 1/2005 | Chapouland et al. | 433/24 |
| 6,857,429 B2 | 2/2005 | Eubank | 128/848 |
| 6,886,566 B2 | 5/2005 | Eubank | 128/859 |
| 6,964,564 B2 | 11/2005 | Phan et al. | 433/6 |
| 7,011,517 B2 | 3/2006 | Nicozisis | 433/3 |
| 7,029,275 B2 | 4/2006 | Rubbert et al. | 433/24 |
| 7,037,108 B2 | 5/2006 | Chishti et al. | 433/24 |
| 7,040,896 B2 | 5/2006 | Pavlovskaia et al. | 433/215 |
| 7,056,115 B2 | 6/2006 | Phan et al. | 433/24 |
| 7,059,850 B1 | 6/2006 | Phan et al. | 433/24 |
| 7,063,533 B2 | 6/2006 | Phan et al. | 433/24 |
| 7,074,038 B1 | 7/2006 | Miller | 433/24 |
| 7,077,647 B2 | 7/2006 | Choi et al. | 433/213 |
| 7,092,784 B1 | 8/2006 | Simkins | 700/163 |
| 7,104,790 B2 | 9/2006 | Cronauer | 433/6 |
| 7,121,825 B2 | 10/2006 | Chishti et al. | 433/6 |
| 7,125,248 B2 | 10/2006 | Phan et al. | 433/6 |
| 7,134,874 B2 | 11/2006 | Chishti et al. | 433/24 |
| 7,156,661 B2 | 1/2007 | Choi et al. | 433/213 |
| 7,160,110 B2 | 1/2007 | Imgrund et al. | 433/213 |
| 7,172,417 B2 | 2/2007 | Sporbert et al. | 433/24 |
| 7,192,275 B2 | 3/2007 | Miller | 433/24 |
| 7,220,122 B2 | 5/2007 | Chishti | 433/24 |
| 7,320,592 B2 | 1/2008 | Chishti et al. | 433/24 |
| 7,326,051 B2 | 2/2008 | Miller | 433/24 |
| 7,331,783 B2 | 2/2008 | Chishti et al. | 433/24 |
| 7,347,688 B2 | 3/2008 | Kopelman et al. | 433/24 |
| 7,416,407 B2 | 8/2008 | Cronauer | 433/6 |
| 7,434,582 B2 | 10/2008 | Eubank | 128/848 |
| 7,435,083 B2 | 10/2008 | Chishti et al. | 433/24 |
| 7,442,041 B2 | 10/2008 | Imgrund et al. | 433/215 |
| 7,458,812 B2 | 12/2008 | Sporbert et al. | 433/24 |
| 7,476,100 B2 | 1/2009 | Kuo | 433/6 B |
| 7,553,157 B2 | 6/2009 | Abolfathi et al. | 433/6 |
| 7,559,328 B2 | 7/2009 | Eubank | 128/848 |
| 7,578,673 B2 | 8/2009 | Wen et al. | 433/24 |
| 7,590,462 B2 | 9/2009 | Rubbert et al. | 700/98 |
| 7,637,262 B2 | 12/2009 | Bailey | 128/848 |
| 7,641,828 B2 | 1/2010 | Desimone et al. | 264/129 |
| 7,658,610 B2 | 2/2010 | Knopp | 433/6 |
| 7,689,398 B2 | 3/2010 | Cheng et al. | 703/11 |
| 7,717,708 B2 | 5/2010 | Sachdeva et al. | 433/24 |
| 7,771,195 B2 | 8/2010 | Knopp et al. | 433/6 |
| 7,802,987 B1 | 9/2010 | Phan | 433/24 |
| 7,824,180 B2 | 11/2010 | Abolfathi et al. | 433/6 |
| 7,826,646 B2 | 11/2010 | Pavlovskaia et al. | 382/128 |
| 7,841,858 B2 | 11/2010 | Knopp et al. | 433/24 |
| 7,854,609 B2 | 12/2010 | Chen et al. | 433/6 |
| 7,878,801 B2 | 2/2011 | Abolfathi et al. | 433/6 |
| 7,878,804 B2 | 2/2011 | Korytov et al. | 433/24 |
| 7,878,805 B2 | 2/2011 | Moss et al. | 433/24 |
| 7,883,334 B2 | 2/2011 | Li et al. | 433/24 |
| 7,901,207 B2 | 3/2011 | Knopp et al. | 433/6 |
| 7,905,724 B2 | 3/2011 | Kuo et al. | 433/6 |
| 7,914,283 B2 | 3/2011 | Kuo | 433/18 |
| 7,942,672 B2 | 5/2011 | Kuo | 433/215 |
| 7,943,079 B2 | 5/2011 | Desimone et al. | 264/346 |
| 7,957,824 B2 | 6/2011 | Boronvinskih et al. | 700/95 |
| 7,987,099 B2 | 7/2011 | Kuo et al. | 705/2 |
| 8,001,972 B2 | 8/2011 | Eubank | 128/848 |
| 8,021,147 B2 | 9/2011 | Sporbert et al. | 433/24 |
| 8,033,282 B2 | 10/2011 | Eubank | 128/848 |
| 8,038,444 B2 | 10/2011 | Kitching et al. | 433/213 |
| 8,070,487 B2 | 12/2011 | Chishti et al. | 433/24 |
| 8,075,306 B2 | 12/2011 | Kitching et al. | 433/24 |
| 8,099,268 B2 | 1/2012 | Kitching et al. | 703/11 |
| 8,099,305 B2 | 1/2012 | Kuo et al. | 705/3 |
| 8,105,080 B2 | 1/2012 | Chishti et al. | 433/24 |
| 8,123,519 B2 | 2/2012 | Schultz | 433/6 |
| 8,152,518 B2 | 4/2012 | Kuo | 433/6 |

(56) References Cited

U.S. PATENT DOCUMENTS

| | | | |
|---|---|---|---|
| 8,152,523 B2 | 4/2012 | Sporbert et al. | 433/24 |
| 8,235,713 B2 | 8/2012 | Phan et al. | 433/6 |
| 8,272,866 B2 | 9/2012 | Chun et al. | 433/6 |
| 8,275,180 B2 | 9/2012 | Kuo | 382/128 |
| 8,292,617 B2 | 10/2012 | Brandt et al. | 433/6 |
| 8,303,302 B2 | 11/2012 | Teasdale | 433/34 |
| 8,348,665 B2 | 1/2013 | Kuo | 433/24 |
| 8,356,993 B1 | 1/2013 | Marston | 433/24 |
| 8,401,686 B2 | 3/2013 | Moss et al. | 700/98 |
| 8,401,826 B2 | 3/2013 | Cheng et al. | 703/1 |
| 8,439,672 B2 | 5/2013 | Matov et al. | 433/24 |
| 8,439,673 B2 | 5/2013 | Korytov et al. | 433/24 |
| 8,444,412 B2 | 5/2013 | Baughman et al. | 433/6 |
| 8,465,280 B2 | 6/2013 | Sachdeva et al. | 433/24 |
| 8,469,705 B2 | 6/2013 | Sachdeva et al. | 433/24 |
| 8,469,706 B2 | 6/2013 | Kuo | 433/24 |
| 8,496,474 B2 | 7/2013 | Chishti et al. | 433/24 |
| 8,512,037 B2 | 8/2013 | Andreiko | 433/24 |
| 8,517,726 B2 | 8/2013 | Kakavand et al. | 433/6 |
| 8,535,580 B2 | 9/2013 | Puttler et al. | 264/16 |
| 8,562,337 B2 | 10/2013 | Kuo et al. | 433/6 |
| 8,562,338 B2 | 10/2013 | Kitching et al. | 433/24 |
| 8,562,340 B2 | 10/2013 | Chishti et al. | 433/24 |
| 8,636,509 B2 | 1/2014 | Miller | 433/24 |
| 8,636,510 B2 | 1/2014 | Kitching et al. | 433/24 |
| 8,690,568 B2 | 4/2014 | Chapoulaud et al. | 433/24 |
| 8,708,697 B2 | 4/2014 | Li et al. | 433/6 |
| 8,734,149 B2 | 5/2014 | Phan et al. | 433/24 |
| 8,734,150 B2 | 5/2014 | Chishti et al. | 433/24 |
| 8,738,165 B2 | 5/2014 | Cinader, Jr. et al. | 700/98 |
| 8,765,031 B2 | 7/2014 | Li et al. | 264/16 |
| 8,777,611 B2 | 7/2014 | Cios | A61C 13/08 |
| 8,780,106 B2 | 7/2014 | Chishti et al. | A61C 9/004 |
| 8,807,999 B2 | 8/2014 | Kuo et al. | 433/24 |
| 8,858,226 B2 | 10/2014 | Phan et al. | 433/6 |
| 8,864,493 B2 | 10/2014 | Leslie-Martin et al. | A61C 7/08 |
| 8,899,976 B2 | 12/2014 | Chen et al. | A61C 7/00 |
| 8,899,978 B2 | 12/2014 | Kitching et al. | 433/24 |
| 8,930,219 B2 | 1/2015 | Trosien et al. | G06Q 50/24 |
| 8,936,464 B2 | 1/2015 | Kopelman | A61C 7/146 |
| 8,998,608 B2 | 1/2015 | Trosien et al. | A61C 7/00 |
| 8,944,812 B2 | 2/2015 | Kuo et al. | A61C 7/08 |
| 8,961,173 B2 | 2/2015 | Miller | A61C 7/08 |
| 8,986,003 B2 | 3/2015 | Valoir | A61C 7/08 |
| 8,992,215 B2 | 3/2015 | Chapoulaud et al. | A61C 7/00 |
| 9,004,915 B2 | 4/2015 | Moss et al. | A61C 7/08 |
| 9,022,781 B2 | 5/2015 | Kuo et al. | A61C 7/12 |
| 9,026,238 B2 | 5/2015 | Kraemer et al. | A61C 13/0004 |
| 9,060,829 B2 | 6/2015 | Sterental et al. | A61C 7/08 |
| 9,107,722 B2 | 8/2015 | Matov et al. | A61C 7/002 |
| 9,119,691 B2 | 9/2015 | Namiranian et al. | A61C 7/08 |
| 9,161,823 B2 | 10/2015 | Morton et al. | A61C 7/00 |
| 9,161,824 B2 | 10/2015 | Chishti et al. | A61C 7/08 |
| 9,204,942 B2 | 12/2015 | Phan et al. | A61C 7/002 |
| 9,211,166 B2 | 12/2015 | Kuo et al. | A61C 7/00 |
| 9,241,774 B2 | 1/2016 | Li et al. | A61C 7/08 |
| 9,301,814 B2 | 4/2016 | Kaza et al. | A61C 7/002 |
| 9,320,575 B2 | 4/2016 | Chishti et al. | A61C 7/08 |
| 9,326,830 B2 | 5/2016 | Kitching et al. | A61C 7/00 |
| 9,326,831 B2 | 5/2016 | Cheang | A61C 7/146 |
| 9,333,052 B2 | 5/2016 | Miller | A61C 7/002 |
| 9,345,557 B2 | 5/2016 | Anderson et al. | A61C 7/08 |
| 9,351,809 B2 | 5/2016 | Phan et al. | A61C 7/08 |
| 9,364,297 B2 | 6/2016 | Kitching et al. | A61C 7/002 |
| 9,375,300 B2 | 6/2016 | Matov et al. | A61C 19/04 |
| 9,414,897 B2 | 8/2016 | Wu et al. | A61C 13/0004 |
| 9,433,476 B2 | 9/2016 | Khardekar et al. | A61C 7/002 |
| 9,492,245 B2 | 11/2016 | Sherwood et al. | A61C 7/00 |
| 9,820,829 B2 | 11/2017 | Kuo | |
| 9,844,420 B2 | 12/2017 | Cheang | A61C 7/002 |
| 9,922,170 B2 | 3/2018 | Trosien et al. | G06F 19/345 |
| 10,022,204 B2 | 7/2018 | Cheang | A61C 7/002 |
| 10,335,250 B2 | 7/2019 | Wen | A61C 7/002 |
| 10,357,336 B2 | 7/2019 | Wen | A61C 7/002 |
| 10,357,342 B2 | 7/2019 | Falkel | A61C 9/0046 |
| 10,548,690 B2 | 2/2020 | Wen | A61C 7/002 |
| 10,588,723 B2* | 3/2020 | Falkel | A61C 9/0046 |
| 10,631,953 B2 | 4/2020 | Wen | A61C 7/002 |
| 10,642,717 B2 | 5/2020 | Girata, Jr. et al. | G06F 11/3654 |
| 2001/0002310 A1 | 5/2001 | Chishti et al. | 433/24 |
| 2002/0010568 A1 | 1/2002 | Rubbert et al. | 703/6 |
| 2002/0025503 A1 | 2/2002 | Chapoulaud et al. | 433/24 |
| 2002/0042038 A1 | 4/2002 | Miller et al. | 433/24 |
| 2002/0072027 A1 | 6/2002 | Chisti | 433/24 |
| 2002/0094503 A1 | 7/2002 | Chishti et al. | 433/24 |
| 2002/0150859 A1 | 11/2002 | Imgrund et al. | 433/24 |
| 2002/0177108 A1 | 11/2002 | Pavlovskaia et al. | 433/215 |
| 2003/0008259 A1 | 1/2003 | Kuo et al. | 433/6 |
| 2003/0039940 A1 | 2/2003 | Miller | 433/24 |
| 2003/0190576 A1 | 10/2003 | Phan et al. | 433/6 |
| 2003/0207224 A1 | 11/2003 | Lotte | 433/6 |
| 2004/0023188 A1 | 2/2004 | Pavlovskaia et al. | 433/215 |
| 2004/0029068 A1 | 2/2004 | Sachdeva et al. | 433/24 |
| 2004/0038168 A1 | 2/2004 | Choi et al. | 433/24 |
| 2004/0142299 A1 | 7/2004 | Miller | 433/24 |
| 2004/0152036 A1 | 8/2004 | Abolfathi | 433/24 |
| 2004/0166456 A1 | 8/2004 | Chishti et al. | 433/24 |
| 2004/0166462 A1 | 8/2004 | Phan et al. | 433/24 |
| 2004/0166463 A1 | 8/2004 | Wen et al. | 433/24 |
| 2004/0197728 A1 | 10/2004 | Abolfathi et al. | 433/24 |
| 2004/0202983 A1 | 10/2004 | Tricca et al. | 433/215 |
| 2004/0242987 A1 | 12/2004 | Liew et al. | 600/407 |
| 2005/0010450 A1 | 1/2005 | Hultgren et al. | 705/3 |
| 2005/0019721 A1 | 1/2005 | Chishti | 433/24 |
| 2005/0048432 A1 | 3/2005 | Choi et al. | 433/24 |
| 2005/0095552 A1 | 5/2005 | Sporbert et al. | 433/24 |
| 2005/0095562 A1 | 5/2005 | Sporbert et al. | 433/215 |
| 2005/0118555 A1 | 6/2005 | Sporbert et al. | 433/213 |
| 2005/0153255 A1 | 7/2005 | Sporbert et al. | 433/24 |
| 2005/0192835 A1 | 9/2005 | Kuo et al. | 705/2 |
| 2005/0244782 A1 | 11/2005 | Chishti et al. | 433/24 |
| 2005/0271996 A1 | 12/2005 | Sporbert et al. | 433/24 |
| 2006/0003283 A1 | 1/2006 | Miller et al. | 433/24 |
| 2006/0035197 A1 | 2/2006 | Hishimoto | 433/212.1 |
| 2006/0068353 A1 | 3/2006 | Abolfathi et al. | 433/6 |
| 2006/0078840 A1 | 4/2006 | Robson | 433/6 |
| 2006/0078841 A1 | 4/2006 | Desimone et al. | 433/6 |
| 2006/0093982 A1 | 5/2006 | Wen | 433/6 |
| 2006/0099546 A1 | 5/2006 | Bergersen | 433/6 |
| 2006/0115785 A1 | 6/2006 | Li et al. | 433/80 |
| 2006/0147872 A1 | 7/2006 | Andreiko | 433/24 |
| 2006/0177789 A1 | 8/2006 | O'Bryan | 433/6 |
| 2006/0188834 A1 | 8/2006 | Hilliard | 433/24 |
| 2006/0199142 A1 | 9/2006 | Liu et al. | 433/24 |
| 2006/0223022 A1 | 10/2006 | Solomon | 433/6 |
| 2006/0223023 A1 | 10/2006 | Lai et al. | 433/24 |
| 2006/0275731 A1 | 12/2006 | Wen et al. | 433/24 |
| 2007/0003907 A1 | 1/2007 | Chishti et al. | 433/217.1 |
| 2007/0238065 A1 | 10/2007 | Sherwood et al. | 433/24 |
| 2007/0283967 A1 | 12/2007 | Bailey | 128/848 |
| 2008/0032248 A1 | 2/2008 | Kuo | 433/6 |
| 2008/0044786 A1 | 2/2008 | Kalili | 433/6 |
| 2008/0050692 A1 | 2/2008 | Hilliard | 433/24 |
| 2008/0051650 A1 | 2/2008 | Massie et al. | 600/425 |
| 2008/0057461 A1 | 3/2008 | Cheng et al. | 433/24 |
| 2008/0057462 A1 | 3/2008 | Kitching et al. | 433/24 |
| 2008/0076086 A1 | 3/2008 | Kitching et al. | 433/24 |
| 2008/0085487 A1 | 4/2008 | Kuo et al. | 433/24 |
| 2008/0118882 A1 | 5/2008 | Su | 433/2 |
| 2008/0141534 A1 | 6/2008 | Hilliard | 29/896.11 |
| 2008/0182220 A1 | 7/2008 | Chishti et al. | 433/24 |
| 2008/0206702 A1 | 8/2008 | Hedge et al. | 433/24 |
| 2008/0215176 A1 | 9/2008 | Borovinskih et al. | 700/117 |
| 2008/0233530 A1 | 9/2008 | Cinader | 433/9 |
| 2008/0248438 A1 | 10/2008 | Desimone et al. | 433/6 |
| 2008/0248443 A1 | 10/2008 | Chisti et al. | 433/24 |
| 2008/0261165 A1 | 10/2008 | Steingart et al. | 433/24 |
| 2008/0268400 A1 | 10/2008 | Moss et al. | 433/24 |
| 2008/0280247 A1 | 11/2008 | Sachdeva et al. | 433/24 |
| 2008/0305451 A1 | 12/2008 | Kitching et al. | 433/24 |
| 2008/0305453 A1 | 12/2008 | Kitching et al. | 433/24 |
| 2009/0081604 A1 | 3/2009 | Fisher | 433/24 |

(56) References Cited

U.S. PATENT DOCUMENTS

| | | | |
|---|---|---|---|
| 2009/0191502 A1 | 7/2009 | Cao et al. | 433/24 |
| 2009/0269714 A1 | 10/2009 | Knopp | 433/24 |
| 2009/0280450 A1 | 11/2009 | Kuo | 433/9 |
| 2009/0291407 A1 | 11/2009 | Kuo | 433/24 |
| 2009/0291408 A1 | 11/2009 | Stone-Collonge et al. | 433/24 |
| 2010/0036682 A1 | 2/2010 | Trosien et al. | 705/3 |
| 2010/0055635 A1 | 3/2010 | Kakavand | 433/6 |
| 2010/0138025 A1 | 6/2010 | Morton et al. | 700/104 |
| 2010/0167225 A1 | 7/2010 | Kuo | 433/24 |
| 2010/0173266 A1 | 7/2010 | Lu et al. | 433/215 |
| 2010/0179789 A1 | 7/2010 | Sachdeva et al. | 703/1 |
| 2010/0280798 A1 | 11/2010 | Pattijn et al. | 703/1 |
| 2011/0005527 A1 | 1/2011 | Andrew et al. | 128/848 |
| 2011/0015591 A1 | 1/2011 | Hanson et al. | 604/318 |
| 2011/0020761 A1 | 1/2011 | Kalili | 433/6 |
| 2011/0039223 A1 | 2/2011 | Li | 433/6 |
| 2011/0114100 A1 | 5/2011 | Alvarez et al. | 128/861 |
| 2011/0123944 A1 | 5/2011 | Knopp et al. | 433/24 |
| 2011/0129786 A1 | 6/2011 | Chun et al. | 433/19 |
| 2011/0165533 A1 | 7/2011 | Li et al. | 433/24 |
| 2011/0269092 A1 | 11/2011 | Kuo et al. | 433/6 |
| 2011/0269097 A1 | 11/2011 | Sporbert et al. | 433/24 |
| 2011/0270588 A1 | 11/2011 | Kuo et al. | 703/2 |
| 2011/0281229 A1 | 11/2011 | Abolfathi | 433/24 |
| 2012/0035901 A1 | 2/2012 | Kitching et al. | 703/11 |
| 2012/0123577 A1 | 5/2012 | Chapoulaud et al. | 700/98 |
| 2012/0150494 A1 | 6/2012 | Anderson et al. | 703/1 |
| 2012/0186589 A1 | 7/2012 | Singh | 128/484 |
| 2012/0199136 A1 | 8/2012 | Urbano | 128/848 |
| 2012/0214121 A1 | 8/2012 | Greenberg | 433/24 |
| 2012/0225399 A1 | 9/2012 | Teasdale | 433/24 |
| 2012/0225400 A1 | 9/2012 | Chishti et al. | 433/24 |
| 2012/0225401 A1 | 9/2012 | Kitching et al. | 433/24 |
| 2012/0227750 A1 | 9/2012 | Tucker | 128/848 |
| 2012/0244488 A1 | 9/2012 | Chishti et al. | 433/24 |
| 2012/0270173 A1 | 10/2012 | Pumphrey et al. | 433/6 |
| 2012/0288818 A1 | 11/2012 | Vendittelli | 433/24 |
| 2013/0022255 A1 | 1/2013 | Chen et al. | 382/131 |
| 2013/0052625 A1 | 2/2013 | Wagner | 434/263 |
| 2013/0078593 A1 | 3/2013 | Andreiko | 433/6 |
| 2013/0081271 A1 | 4/2013 | Farzin-Nia et al. | A61C 13/00 |
| 2013/0085018 A1 | 4/2013 | Jensen et al. | 473/404 |
| 2013/0095446 A1 | 4/2013 | Andreiko et al. | 433/6 |
| 2013/0122445 A1 | 5/2013 | Marston | A61C 7/145 |
| 2013/0122448 A1 | 5/2013 | Kitching | A61C 7/002 |
| 2013/0157213 A1 | 6/2013 | Arruda | 433/6 |
| 2013/0201450 A1 | 8/2013 | Bailey et al. | A61B 3/14 |
| 2013/0204583 A1 | 8/2013 | Matov et al. | 703/1 |
| 2013/0230819 A1 | 9/2013 | Arruda | A61C 7/08 |
| 2013/0231899 A1 | 9/2013 | Khardekar et al. | 703/1 |
| 2013/0236848 A1 | 9/2013 | Arruda | A61C 7/08 |
| 2013/0266906 A1 | 10/2013 | Soo | A61C 7/08 |
| 2013/0302742 A1 | 11/2013 | Li et al. | 433/6 |
| 2013/0308846 A1 | 11/2013 | Chen et al. | G06T 7/0012 |
| 2013/0317800 A1 | 11/2013 | Wu et al. | 703/11 |
| 2013/0323665 A1 | 12/2013 | Dinh et al. | A61C 7/08 |
| 2013/0325431 A1 | 12/2013 | See et al. | A61C 7/002 |
| 2014/0023980 A1 | 1/2014 | Kitching et al. | A61C 7/002 |
| 2014/0067335 A1 | 3/2014 | Andreiko | A61C 7/08 |
| 2014/0255864 A1 | 9/2014 | Machata et al. | A61C 7/146 |
| 2014/0358497 A1 | 12/2014 | Kuo et al. | G06F 19/3437 |
| 2014/0363779 A1 | 12/2014 | Kopelman | A61C 7/08 |
| 2014/0370452 A1 | 12/2014 | Tseng | A61C 7/08 |
| 2015/0004553 A1 | 1/2015 | Li et al. | A61C 7/08 |
| 2015/0004554 A1 | 1/2015 | Cao et al. | A61C 7/08 |
| 2015/0018956 A1 | 1/2015 | Steinmann et al. | A61F 2/447 |
| 2015/0025907 A1 | 1/2015 | Trosien et al. | G06F 19/345 |
| 2015/0044623 A1 | 2/2015 | Rundlett | A61C 7/08 |
| 2015/0044627 A1 | 2/2015 | German | A61C 7/002 |
| 2015/0064641 A1 | 3/2015 | Gardner | A61C 7/146 |
| 2015/0093713 A1 | 4/2015 | Chen et al. | A61C 19/066 |
| 2015/0093714 A1 | 4/2015 | Kopelman | A61C 7/146 |
| 2015/0125802 A1 | 5/2015 | Tal | A61C 7/08 |
| 2015/0128421 A1 | 5/2015 | Mason et al. | A61C 7/08 |
| 2015/0157421 A1 | 6/2015 | Martz et al. | A61C 7/08 |
| 2015/0182321 A1 | 7/2015 | Karazivan et al. | A61C 19/003 |
| 2015/0216626 A1 | 8/2015 | Ranjbar | A61C 7/08 |
| 2015/0216627 A1 | 8/2015 | Kopelman | A61C 7/08 |
| 2015/0238280 A1 | 8/2015 | Wu et al. | A61C 7/002 |
| 2015/0238282 A1 | 8/2015 | Kuo et al. | A61C 7/08 |
| 2015/0238283 A1 | 8/2015 | Tanugula et al. | A61C 7/36 |
| 2015/0238284 A1 | 8/2015 | Wu et al. | A61C 7/36 |
| 2015/0245887 A1 | 9/2015 | Izugami et al. | A61C 7/08 |
| 2015/0254410 A1 | 9/2015 | Sterental et al. | G06F 19/345 |
| 2015/0265376 A1 | 9/2015 | Kopelman | A61C 7/08 |
| 2015/0289949 A1 | 10/2015 | Moss et al. | A61C 7/08 |
| 2015/0289950 A1 | 10/2015 | Khan | A61C 7/08 |
| 2015/0305830 A1 | 10/2015 | Howard et al. | A61C 7/002 |
| 2015/0305831 A1 | 10/2015 | Cosse | A61C 7/02 |
| 2015/0320518 A1 | 11/2015 | Namiranian et al. | A61C 7/10 |
| 2015/0320532 A1 | 11/2015 | Matty et al. | A61C 19/066 |
| 2015/0335399 A1 | 11/2015 | Caraballo | A61C 7/08 |
| 2015/0335404 A1 | 11/2015 | Webber et al. | A61C 9/00 |
| 2015/0336299 A1 | 11/2015 | Tanugula et al. | B29C 33/448 |
| 2015/0342464 A1 | 12/2015 | Wundrak et al. | A61B 5/0088 |
| 2015/0351871 A1 | 12/2015 | Chishti et al. | A61C 7/002 |
| 2015/0359609 A1 | 12/2015 | Khan | A61C 7/002 |
| 2015/0366637 A1 | 12/2015 | Kopelman et al. | A61C 7/08 |
| 2015/0366638 A1 | 12/2015 | Kopelman et al. | A61C 7/08 |
| 2016/0000527 A1 | 1/2016 | Arruda | A61C 7/08 |
| 2016/0008095 A1 | 1/2016 | Matov et al. | A61C 7/002 |
| 2016/0008097 A1 | 1/2016 | Chen et al. | A61C 7/08 |
| 2016/0051341 A1 | 2/2016 | Webber | A61C 7/12 |
| 2016/0051342 A1 | 2/2016 | Phan et al. | A61C 7/146 |
| 2016/0051348 A1 | 2/2016 | Boerjes et al. | A61C 13/0004 |
| 2016/0067013 A1 | 3/2016 | Morton et al. | A61C 7/002 |
| 2016/0067014 A1 | 3/2016 | Kottemann et al. | A61C 7/008 |
| 2016/0074137 A1 | 3/2016 | Kuo et al. | A61C 7/002 |
| 2016/0074138 A1 | 3/2016 | Kitching et al. | A61C 7/002 |
| 2016/0094670 A1 | 3/2016 | Garcia Manchado | H04L 67/22 |
| 2016/0095668 A1 | 4/2016 | Kuo et al. | A61C 7/002 |
| 2016/0106521 A1 | 4/2016 | Tanugula et al. | A61C 7/08 |
| 2016/0120617 A1 | 5/2016 | Jinkyun | A61C 7/002 |
| 2016/0120621 A1 | 5/2016 | Li et al. | A61C 7/08 |
| 2016/0128803 A1 | 5/2016 | Webber et al. | A61C 7/08 |
| 2016/0135924 A1 | 5/2016 | Choi et al. | A61C 7/002 |
| 2016/0135926 A1 | 5/2016 | Djamchidi | A61C 7/002 |
| 2016/0135927 A1 | 5/2016 | Boltunov et al. | A61C 7/002 |
| 2016/0157961 A1 | 6/2016 | Lee | A61C 7/002 |
| 2016/0175068 A1 | 6/2016 | Cai et al. | A61C 7/002 |
| 2016/0175069 A1 | 6/2016 | Korytov et al. | A61C 7/002 |
| 2016/0184129 A1 | 6/2016 | Liptak et al. | A61F 5/566 |
| 2016/0193014 A1 | 7/2016 | Morton et al. | A61C 7/08 |
| 2016/0199216 A1 | 7/2016 | Cam et al. | A61F 5/566 |
| 2016/0203604 A1 | 7/2016 | Gupta et al. | G06T 7/0014 |
| 2016/0206402 A1 | 7/2016 | Kitching et al. | A61C 7/002 |
| 2016/0256240 A1 | 9/2016 | Shivapuja et al. | A61C 7/08 |
| 2016/0310235 A1 | 10/2016 | Derakhshan et al. | A61C 7/002 |
| 2016/0338799 A1 | 11/2016 | Wu et al. | A61C 7/002 |
| 2016/0367339 A1 | 12/2016 | Khardekar et al. | A61C 7/002 |
| 2017/0007359 A1 | 1/2017 | Kopelman et al. | A61C 7/002 |
| 2017/0100207 A1 | 4/2017 | Wen | A61C 7/002 |
| 2017/0100208 A1 | 4/2017 | Wen | A61C 7/002 |
| 2017/0100209 A1 | 4/2017 | Wen | A61C 7/002 |
| 2017/0100210 A1 | 4/2017 | Wen | A61C 7/002 |
| 2017/0100211 A1 | 4/2017 | Wen | A61C 7/002 |
| 2017/0100214 A1 | 4/2017 | Wen | A61C 7/002 |
| 2017/0325911 A1 | 11/2017 | Marshall | A61C 7/146 |
| 2018/0014912 A1 | 1/2018 | Radmand | A61C 5/007 |
| 2018/0042708 A1 | 2/2018 | Caron et al. | A61C 13/0004 |
| 2018/0078335 A1 | 3/2018 | Falkel | A61C 7/002 |
| 2018/0078343 A1 | 3/2018 | Falkel | A61C 7/36 |
| 2018/0078344 A1 | 3/2018 | Falkel | A61C 7/36 |
| 2018/0078347 A1 | 3/2018 | Falkel | A61C 9/0046 |
| 2018/0092714 A1 | 4/2018 | Kitching et al. | A61C 7/002 |
| 2018/0092715 A1 | 4/2018 | Kitching et al. | A61C 7/002 |
| 2018/0158544 A1 | 6/2018 | Trosien et al. | G16H 15/00 |
| 2018/0168781 A1 | 6/2018 | Kopelman et al. | A61C 1/0015 |
| 2019/0008612 A1 | 1/2019 | Kitching et al. | A61C 7/00 |
| 2019/0046297 A1 | 2/2019 | Kopelman et al. | A61C 7/146 |
| 2019/0321135 A1 | 10/2019 | Wen | A61C 7/002 |
| 2019/0343602 A1 | 11/2019 | Wen | A61C 7/08 |
| 2019/0358002 A1 | 11/2019 | Falkel | A61C 9/0046 |
| 2020/0146775 A1 | 5/2020 | Wen | A61C 7/002 |

(56) References Cited

U.S. PATENT DOCUMENTS

| | | | |
|---|---|---|---|
| 2020/0205936 A1 | 7/2020 | Wen | A61C 7/002 |
| 2020/0253693 A1 | 8/2020 | Wen | A61C 7/002 |
| 2020/0345459 A1 | 11/2020 | Schueller et al. | A61C 7/146 |

FOREIGN PATENT DOCUMENTS

| | | | | |
|---|---|---|---|---|
| CN | 101528152 B | 12/2012 | | A61C 7/00 |
| CN | 103932807 A | 7/2014 | | A61C 7/00 |
| EP | 1474062 B1 | 4/2011 | | A61C 7/00 |
| EP | 2056734 B1 | 9/2015 | | A61C 7/00 |
| EP | 2957252 A1 | 12/2015 | | A61C 7/14 |
| JP | 2005-515826 A | 6/2005 | | A61C 7/00 |
| JP | 2006-500999 A | 1/2006 | | A61C 19/04 |
| JP | 2009-202031 A | 9/2009 | | A61C 7/00 |
| JP | 4323322 B2 | 9/2009 | | A61C 7/00 |
| JP | 2010-502246 A | 1/2010 | | A61C 7/00 |
| JP | 4566746 B2 | 10/2010 | | A61C 7/00 |
| JP | 2012-139540 A | 7/2012 | | A61C 7/14 |
| JP | 5015197 B2 | 8/2012 | | A61C 7/00 |
| JP | 5015765 B2 | 8/2012 | | A61C 7/00 |
| JP | 5149898 B2 | 2/2013 | | A61C 7/00 |
| JP | 5291218 B2 | 9/2013 | | A61C 7/00 |
| JP | 2007-525289 A | 9/2017 | | A61C 7/00 |
| KR | 10-1450866 B1 | 10/2014 | | G06Q 50/22 |
| WO | WO 2001/082192 A1 | 11/2001 | | G06F 17/60 |
| WO | WO 2002/047571 A3 | 6/2002 | | A61C 3/00 |
| WO | WO 2003/063721 A1 | 8/2003 | | A61C 5/00 |
| WO | WO 2004/028391 A3 | 4/2004 | | A61C 3/00 |
| WO | WO 2005/086058 A1 | 9/2005 | | G06F 17/60 |
| WO | WO 2004/098379 A3 | 11/2005 | | A61C 3/00 |
| WO | WO 2006/050452 A2 | 5/2006 | | A61C 3/00 |
| WO | WO 2006/096558 A2 | 9/2006 | | A61C 3/00 |
| WO | WO 2008/026064 A3 | 3/2008 | | A61C 7/00 |
| WO | WO 2008/102132 A1 | 8/2008 | | A61C 7/08 |
| WO | WO 2008/149222 A3 | 12/2008 | | A61C 7/00 |
| WO | WO 2009/068892 A1 | 6/2009 | | A61C 9/00 |
| WO | WO 2016/004415 A1 | 1/2016 | | A61F 5/56 |
| WO | WO 2016/100577 A1 | 6/2016 | | A61C 7/00 |
| WO | WO 2017/062207 A1 | 4/2017 | | A61C 3/00 |
| WO | WO 2017/062208 A1 | 4/2017 | | A61C 3/00 |
| WO | WO 2017/062209 A1 | 4/2017 | | A61C 3/00 |
| WO | WO 2017/062210 A1 | 4/2017 | | A61C 7/00 |
| WO | WO 2018/057622 A1 | 3/2018 | | A61C 7/08 |
| WO | WO 2018/118200 A1 | 6/2018 | | A61C 7/00 |
| WO | WO 2020/222905 A1 | 11/2020 | | A61C 7/02 |
| WO | WO 2020/223384 A1 | 11/2020 | | A61C 7/08 |

* cited by examiner

DIGITAL DENTAL EXAMINATION AND DOCUMENTATION

CROSS-REFERENCE TO RELATED APPLICATIONS

This application is a continuation of application Ser. No. 16/435,028 filed Jun. 7, 2019, which is a continuation of U.S. patent application Ser. No. 15/710,469 filed Sep. 20, 2017 (now U.S. Pat. No. 10,357,342), which claims the benefit of U.S. Provisional Application No. 62/397,504 filed Sep. 21, 2016, and U.S. Provisional Application No. 62/397,525, filed Sep. 21, 2016, the contents of which are incorporated herein by reference in their entireties for all purposes.

BACKGROUND

1. Technical Field

This disclosure relates generally to the field of electronic dental examination and documentation and more specifically to systems and methods that can electronically evaluate detected oral features and document the results.

2. Background of the Art

Comprehensive dental examinations should be a very thorough, detailed, and well-documented procedure. However, due to the rigors associated with the volume of information that accompanies dental examinations, it is well known that dentists often do not complete a thorough examination and/or do not adequately document their findings and observations. It is generally known as well that dental examinations can and should include the evaluation of periodontal tissues and functional deficiencies in addition to dental structures and diseases. However, functional deficiencies and periodontal structures are often overlooked due to the difficulty in quantifying them or being able to map them over time.

Previous efforts to improve this field have more narrowly focused on diagnosing other dental problems (i.e., those other than functional deficiencies and/or those unrelated to periodontal tissues), patient education of the problems, helping the patient understand the problems, determining the extent of the problems, and making future prognoses. However, those efforts have all come up short with respect to electronic analysis of acquired (e.g., scanned, photographed) dental data to identify, quantify, map, and define the extent of dental structures, diseases and deficiencies, especially in relation to functional deficiencies and periodontal structures. The current state of the art is for a dentist to make note of a condition, visually estimate the extent of the problem, and then decide to either treat or monitor the condition, for example, by looking at scan results or radiographs on a computer screen. However, if the dentist decides to monitor the condition (as opposed to treating it), there is no way for the dentist to accurately determine if the problem is progressing or has progressed at the patient's next dental exam other than going by the patient's symptoms or a change in radiographs.

Therefore, a solution is needed for systems and methods that can accurately diagnose conditions associated with hard and soft dental tissues alike, including dental structures, diseases, and deficiencies, and which can evaluate, quantify and/or map such conditions, including periodontal structures and/or functional deficiencies. Such a solution should be able to quantify and map the extent of these conditions and estimate the quantity of tooth substance loss at the time of the exam or historically over time. Such a solution should also be able to process data from dental data acquisition devices (e.g., from scanners) to analyze and determine the extent of the conditions (e.g., the extent of the tooth substance loss) as well as give an accurate appraisal of the quantity of tooth substance loss (e.g., the mass or volume of the loss). Such solutions are needed to provide accurate electronic dental records and comprehensively diagnose all existing conditions. A need exists to improve the programming of current processors so that such data analysis is possible. A need also exists for systems and methods that can execute both a physiologic and functional analysis of dental tissues and structures from acquired data.

BRIEF SUMMARY OF THE INVENTION

This disclosure relates generally to electronic dental examination and documentation.

More specifically, systems and methods are disclosed that can electronically evaluate detected oral features and analyze and document the results.

Briefly, systems and methods are disclosed that utilize digitally gathered information (e.g., from scans, radiographs, photographs, or any combination thereof) to identify and document existing dental structures, diseases and deficiencies for use in baseline documentation, historical mapping, comparisons to the norm, diagnosis, prognosis, treatment planning and data libraries, and for the creation of comprehensive electronic dental records.

The methods disclosed can include methods for electronically diagnosing and tracking the progression of one or more dental conditions. For example, a method is disclosed that can include acquiring a first oral feature in a first data acquisition using a data acquisition device. The method can include determining a first oral feature first reference point from the first data acquisition. Determining the first oral feature first reference point can include using a processor. The method can include diagnosing a first dental condition upon confirming that the first oral feature first reference point is associated with the first dental condition. The method can include acquiring the first oral feature in a second data acquisition using the data acquisition device. The method can include determining a first oral feature second reference point from the second data acquisition. Determining the first oral feature second reference point can include using the processor. The method can include tracking the progression of the first dental condition by determining a discrepancy between the first oral feature first and second reference points.

The methods disclosed can include methods for electronically diagnosing and tracking the progression of one or more dental conditions. For example, a method is disclosed that can include determining a dental condition first reference point and a dental condition second reference point. Determining the dental condition first and second reference points can include processing first and second data sets, respectively, received from a data acquisition device. The method can include diagnosing the dental condition upon confirming that the dental condition first and/or second reference point is associated with the dental condition. The method can include tracking the progression of the dental condition by determining a discrepancy between the dental condition first and second reference points.

The systems disclosed can include dental condition diagnosis and tracking systems. For example, a system is disclosed that can include a data acquisition device. The system can include an examination unit. The examination unit can be configured to process first and second data sets received from the data acquisition device to determine a dental condition first reference point and a dental condition second reference point, respectively. The examination unit can be configured to diagnose the dental condition upon confirming that the dental condition first and/or second reference point is associated with the dental condition. The examination unit can be configured to track the progression of the dental condition by determining a discrepancy between the dental condition first and second reference points.

BRIEF DESCRIPTION OF THE DRAWINGS

The drawings shown and described are exemplary embodiments and non-limiting.

Like reference numerals indicate identical or functionally equivalent features throughout.

DETAILED DESCRIPTION

Figure 1:
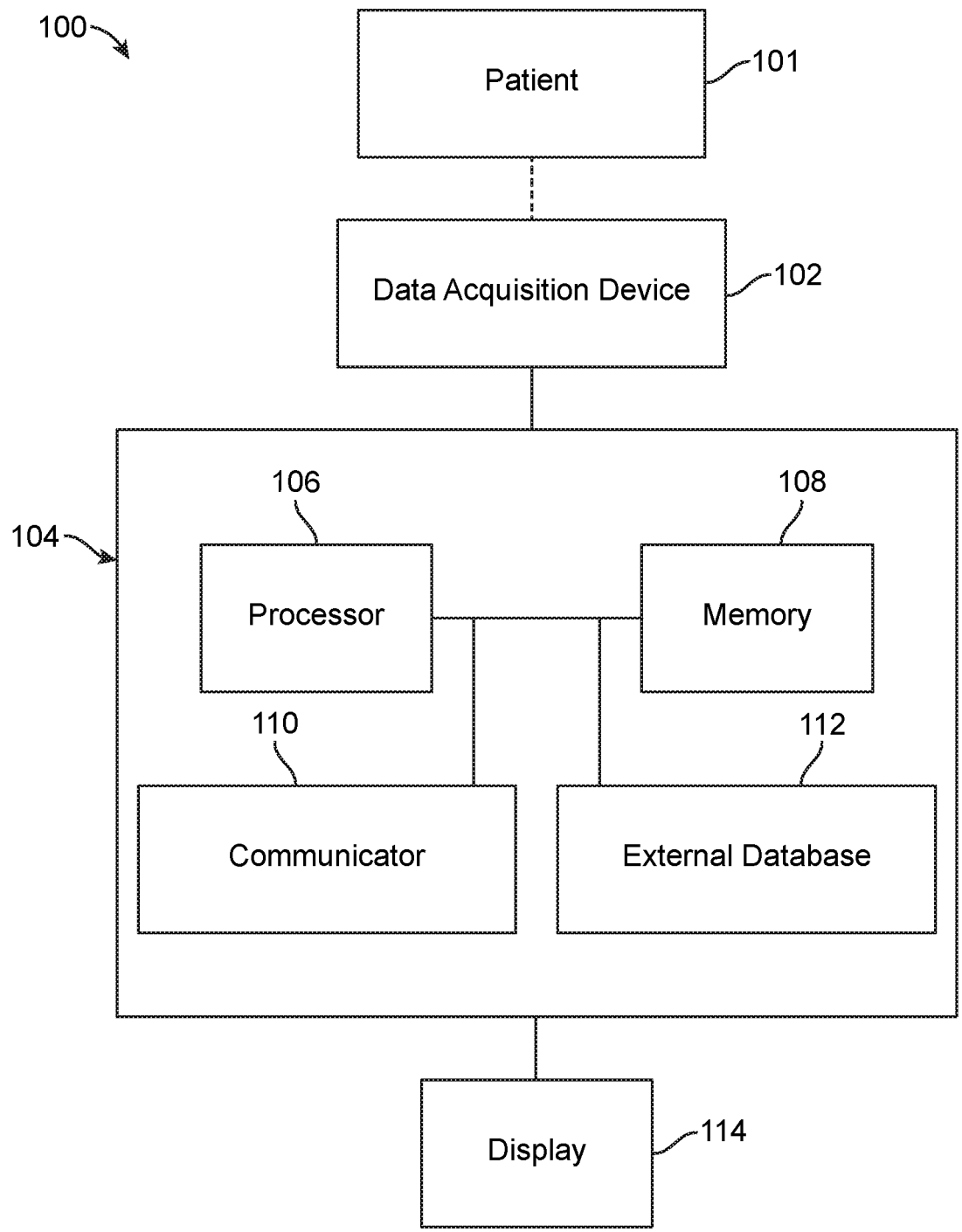
FIG. 1 illustrates a schematic of a variation of an electronic dental examination and documentation system.

Systems and methods are disclosed that can electronically evaluate and document oral features, including dental features, periodontal features, craniofacial features, or any combination thereof. The systems and methods disclosed can examine, analyze, diagnose and document dental structures, deficiencies, and/or diseases, as well as any other condition relating thereto, for example, any condition relating to the masticatory system. Dental structures, deficiencies and diseases are individually and collectively referred to throughout as features and conditions.

The systems and methods disclosed can identify, quantify, analyze and/or map existing conditions, predict the progression of existing conditions, provide a probability for the manifestation of currently non-manifested conditions, provide a recommendation to treat and/or monitor existing conditions, provide a recommendation to treat and/or monitor not yet manifested conditions (e.g., with preventative treatment), identify variables that are contributing to and causing the development of existing and not yet manifested conditions, identify educational protocols that can influence and succeed in changing patient behavior that is causing or is detrimental to dental health or its improvement, identify educational protocols most likely to influence and succeed in changing behavior that is causing or is detrimental to dental health or its improvement specific to the patient, for example, based partly or completely on physiologic, genetic, bacterial, and environmental factors, as well as their health history, or any combination thereof. For example, the systems and methods disclosed can measure, map, diagnose, and/or define the extent of dental deficiencies as well as any other detectable (e.g., scannable, photographable) dental conditions. The mappings disclosed can be visual (e.g., using one-, two-, three-, and/or four-dimensional representations) and/or numeric (e.g., using numbers, ratios, and/or matrices). Three- and four-dimensional representations, for example, can be 3D printed structures and/or 3D computer renderings, with the four-dimensional printed structures and/or renderings including time and/or date indicators. The mappings disclosed can be used to create historical, current, and/or predictive models for the acquired (e.g., scanned, x-rayed, photographed) conditions and/or of healthy structures not associated with a condition.

The systems and methods disclosed can perform structural, physiological, and/or functional analyses of existing conditions. The systems and methods disclosed can analyze data captured from one or multiple data acquisition devices (e.g., one or multiple scanning devices, image capturing devices, video capturing devices, or any combination thereof) and/or systems. For example, the systems and methods disclosed can analyze data recorded by one or multiple intra-oral data acquisition devices (e.g., one or multiple intra-oral scanners, radiograph devices, camera devices, or any combination thereof).

The methods disclosed can include algorithms that can be executed by the system. The algorithms disclosed can use data recorded by and/or retrieved from the one or multiple data acquisition devices and/or from a database, memory, or other storage medium that has the recorded data stored thereon. The algorithms disclosed can measure or otherwise quantify the extent of the areas affected by a condition. The algorithms disclosed can measure or otherwise quantify the extent of the conditions on one or more teeth, for example, on each tooth individually and/or on multiple teeth sequentially and/or simultaneously. The resultant data can be used visually on the existing image or digital representation (e.g., by superimposing the data or a derivative of it on the existing image or digital representation) and/or can be used in a numeric formulation on a tooth-by-tooth and/or entire dentition summary. For example, the resultant data can be used visually on an existing scan (e.g., a previous scan obtained at an earlier patient visit), for example, by superimposing the data or a derivative of it on the earlier acquired scan.

The systems and methods disclosed can electronically document or otherwise store examination and/or analysis results for use in baseline documentation, mapping (e.g., historical mapping, current mapping, predictive mapping), statistical comparisons (e.g., comparisons to the norm), diagnosis, treatment planning, patient education, or any combination thereof. The electronically documented or otherwise stored data can be queried or otherwise retrieved during the evaluation and analysis of subsequent data acquisitions (e.g., scans, radiographs, photographs) to be able to accurately determine the progression of the previously examined conditions, for example, by comparing results of a subsequent data acquisition to the results of one or more previous data acquisitions. The results of a data acquisition (e.g., the initial data acquisition and/or one or more subsequent data acquisitions) can be compared to results previously obtained from the same patient and/or from one or more different patients. The system and methods disclosed can have and/or can build a library of patient-specific and non-patient specific examination and analysis data. Such libraries of data can allow one-time data acquisitions and/or each subsequent data acquisition to be more informative to the patient and medical professional alike. The electronically stored data can allow the system to build dental narratives for one or multiple teeth that can be quickly referenced and provide critical details regarding a person's health that visual inspection of data acquisition results would not provide alone.

The systems and methods disclosed can utilize artificial intelligence and/or machine learning when processing acquired data (e.g., scan data, radiographic data, photograph data), including programming one or more processors with artificial intelligence and/or machine learning software.

In this way, the systems and methods disclosed can provide comprehensive dental examinations that are both accurate and reliable, and which enable existing and not yet manifested conditions to be more easily, accurately, and precisely tracked over time.

The various exemplary variations of the systems and methods disclosed can be interchangeably combined with any other variation disclosed and contemplated herein. Likewise, the various components, features, elements, processes, steps, and/or operations of each exemplary system and/or method disclosed can be interchangeably combined with any other variation disclosed and contemplated herein Although every iteration of the systems and methods disclosed has not been expressly illustrated in the accompanying figures, it will be understood that the accompanying figures are exemplary and non-limiting, and that while absence of a feature does not require its omission, it nevertheless discloses its omission, and hereby provides support for potential future negative limitations in the claims. Any disclosure herein can be combined or modified with any other disclosure herein, even if such a combination is not expressly illustrated in the accompanying figures, as the accompanying figures are exemplary only.

System

FIG. 1 illustrates a schematic of a variation of an electronic dental examination and documentation system 100. The system 100 can have a data acquisition device 102 and an examination unit 104. The data acquisition device 102 can be in wired or wireless communication with the examination unit 104. One or more data acquisition devices 102 can be connected to the examination unit 104. The examination unit 104 can receive data from one or more data acquisition devices 102, for example, separately, sequentially, and/or simultaneously. The data acquisition device 102 can be used to capture or image (e.g., scan, photograph, x-ray) the various oral features disclosed herein, including dental features, periodontal features, craniofacial features, or any combination thereof, including the various hard and soft tissues associated with each. FIG. 1 illustrates that the data acquisition device 102 can acquire the oral features of a patient 101, for example, by electronically capturing or imaging the oral features. The acquiring is indicated by the dotted line that extends between the patient 101 and the data acquisition device 102. The dotted line also represents wired or wireless data transfer to and/or from the data acquisition device 102 and the examination unit 104.

The data acquisition device 102 can be used to create a digital impression of all or part of an oral cavity and the masticatory system. For example, the digital data that the data acquisition device 102 acquires can digitally represent one or more oral features, including the entire dentition, a subset thereof, a single tooth, one or more portions of multiple teeth, a portion of a single tooth, the supporting periodontal and/or craniofacial structures, nerve innervation, blood vessel perfusion, or any combination thereof. In this way, the data acquisition device 102 can be used to digitally record the existing conditions of an oral cavity and the masticatory system, including healthy and unhealthy conditions, as well as conditions that are improving or deteriorating.

The data acquired by one or multiple data acquisition devices 102 can be merged or otherwise combined into a single digital representation (e.g., image), can be kept separate, or can be partitioned and/or combined into multiple digital representations (e.g., images). One or more aspects (e.g., one or more dental features or conditions) recorded by one or multiple data acquisition devices 102 can be merged or otherwise combined into a single digital representation (e.g., an image), can be kept separate, or can be partitioned and/or combined into multiple digital representations (e.g., images). For example, multiple data sets acquired by one or multiple data acquisition devices 102 can be merged or otherwise combined into a single digital representation (e.g., image), can be kept separate, or can be partitioned and/or combined into multiple digital representations (e.g., images), as can multiple data sets representative of one or more aspects (e.g., one or more dental features or conditions) recorded by one or multiple data acquisition devices 102.

The data acquisition device 102 can be a scanner, an x-ray device, a camera, or any combination thereof. For example, the data acquisition device 102 can be a handheld scanner, radiographic imaging device, camera, or any combination thereof. Additionally or alternatively, the data acquisition device 102 can be a scanner, radiographic imaging device, or camera mountable (e.g., mounted) to a wall, floor, and/or ceiling. For example, the system 100 can have or can be capable of utilizing (e.g., receiving data recorded by) one or multiple intra-oral scanners, and/or one or multiple other data acquisition devices. The data acquisition device 102 can be a 3D scanner (e.g., 3D video scanner), a computed tomography (CT) scanner, a confocal imaging scanner, a parallel confocal imaging scanner, a light emitting diode (LED) pattern projection scanner, a laser scanner, a radiographic scanner, or any combination thereof. One or multiple (e.g., two, three, four or more) types of data acquisition devices 102 can be used to acquire dental data for dental condition detection and evaluation. The number and type of data acquisition devices 102 used can depend on the conditions that are sought to be detected, for example, whether soft and/or hard tissues need to be detected, such that the number and type used can advantageously be made on a case-by-case basis to accommodate each person's needs.

The data acquisition device 102 can record digital data having one or multiple images, data slices, and/or videos. The data acquisition device 102 can provide data having any file format, for example, stereolithography (STL) files, DCM files having a DICOM format, graphic interchange format (GIF) files, joint photographic experts group (JPEG) files, tagged image files (TIF), and/or portable network graphics (PNG) files. Such data cannot be prepared in the mind of a dentist and therefore provides more accurate and reliable results than when compared to visual inspection alone.

The examination unit 104 can process data received and/or retrieved from the data acquisition device 102. For example, the examination unit 104 can process images and videos or any other processable representation recorded by the data acquisition device 102. The examination unit 104 can process videos and/or slice video data into one or more smaller sized still images. The examination unit 104 can process acquired data in real-time and/or can process acquired data that was previously stored, for example, in a computer readable storage medium.

The one or more data acquisition devices 102 and the examination unit 104 can provide a comprehensive electronic examination of one or multiple patients (e.g., patient 101).

The examination unit 104 can be local or remote relative to the data acquisition device 102. For example, the examination unit 104 can be on or be part of a server such as a cloud server, a cluster server, and/or a storage server. The examination unit 104 can analyze data from one or multiple data acquisition devices 102 and can be configured to store raw data (e.g., unprocessed data, unanalyzed data), processed data, data derived from raw and/or processed data, or any combination thereof, for example, on a server or on a local memory medium. In this way, the examination unit 104 can electronically "document" examination results and any analyses thereof that can be later referenced by the patient, a medical professional (e.g., dentist), the data acquisition device 102, and/or the examination unit 104. Such storage can be useful for establishing an initial baseline data acquisition that can be analyzed to determine one or more reference points that can be stored to later compare to one or more reference points of one or more subsequent data acquisitions (e.g., scans, radiographs, photographs), thereby enabling electronic tracking and observation of the dentition, the support structures and surrounding tissues, and the conditions, diseases, and/or conditions thereof. The references points can be numerical or visual representations. For example, the reference points can be one or more of the quantifications and/or mappings described herein (e.g., reference locations, reference measurements, reference shapes, reference ratios, reference colors, shades, or tints, reference blood perfusion, or any combination thereof).

FIG. 1 further illustrates that the examination unit 104 can have a processing unit 106, a memory unit 108, and a communication unit 110. The processing unit 106 can be coupled to the memory and communication units 108, 110 through high-speed buses.

The processing unit 106 can include one or more central processing units (CPUs), graphical processing units (GPUs), application-specific integrated circuits (ASICs), field-programmable gate arrays (FPGAs), or any combination thereof. The processing unit 106 can execute software stored in the memory unit 108 to execute the methods, instructions, and/or algorithms described herein. The processing unit 106 can be implemented in a number of different manners. For example, the processing unit 106 can be an embedded processor, a processor core, a microprocessor, a logic circuit, a hardware finite state machine (FSM), a digital signal processor (DSP), or any combination thereof. As a more specific example, the processing unit 104 can be a 32-bit or a 64-bit processor.

The memory unit 108 can store software, data, logs, or any combination thereof. The data stored can be raw data, processed data, data derived from raw and/or processed data, or any combination thereof. For example, the memory unit 108 can store data received from the data acquisition device 102, as well as the output from the processing unit 106 after the data acquisition device 102 data has been analyzed and/or modeled. The memory unit 108 can be an internal memory of the examination unit 104 as shown in FIG. 1, or it can be an external memory, such as a memory residing on a storage node, a cloud server, and/or a storage server.

The memory unit 108 can be a volatile memory or a non-volatile memory. For example, the memory unit 108 can be a non-volatile storage medium such as non-volatile random access memory (NVRAM), flash memory, disk storage, or a volatile storage such as static random access memory (SRAM). The memory unit 108 can be the main storage unit for the examination unit 104.

The communication unit 110 can include one or more wired or wireless communication interfaces. For example, the communication unit 110 can be a network interface card of the examination unit 104. The communication unit 110 can be a wireless modem or a wired modem, for example, a WiFi modem, a 3G modem, a 4G modem, an LTE modem. Alternatively, or in combination, the communication unit 110 can be a Bluetooth™ component, a radio receiver, an antenna, or any combination thereof. For example, the communication unit 110 can be a server communication unit. The examination unit 104 can transmit and/or receive data packets and/or messages using the communication unit 110. The communication unit 110 can connect to or communicatively couple with one or more wireless signal transceivers and/or networks.

The examination unit 104 can include an external database 112 separate from, alternative to, and/or additional to the memory 108. The memory 108 and/or the database 112 can be internal and/or external to the examination unit 104, and can each be non-volatile and/or volatile memory. Alternatively, or in combination, the database 112 can be integrated or otherwise combined with the memory 108. The external database 112 can be on or be part of a server, for example, a cloud server, and/or a storage server.

The memory 108 and/or the external database 112 can be configured to store patient-specific data and/or non-patient specific data. For example, the memory 108 can store patient-specific data and the external database 112 can store non-patient specific data recorded from one or more patients different from patient 101.

The examination unit 104 can have one or multiple processing units 106, memories 108, communication units 110, and/or external databases 112.

FIG. 1 also illustrates that the system 100 can have one or more displays 114. The display 114 can display data acquisition results and/or the analyses and mappings thereof. The display 114 can be integrated with the device or system having the examination unit 104 and/or can be part of a standalone device in wired or wireless communication with the examination unit 104. For example, the display 114 can be part of a computer, a smartphone, a tablet, a laptop, a smartwatch, or any combination thereof. The device having the display 114 can be in communication with the data acquisition device 102, one or more other devices, the cloud, and/or one or more networks.

Alternatively, or in combination, the examination unit 104 can be part of or integrated with the device or system having the display 114, including a personal or portable device, for example, a computer, a smartphone, a tablet, a laptop, a smartwatch, or any combination thereof. Executable code can be installed on memory (e.g., memory 108) of the device having the display 114. When the executable code is executed by the device, the device can perform the instructions, processes, methods, and operations disclosed and contemplated herein, such that the device can analyze data acquisition results. For example, a smartphone application can be downloaded onto a smartphone that has executable code configured to carry out the various functions of the examination unit 104. Alternatively, or in combination, executable code can be located on the cloud, for example, on a server. The device (e.g., a smartphone) can query the server to run the executable code on the server to carry out the instructions, processes, methods, and operations disclosed and contemplated herein.

Alternatively, or in combination, the examination unit 104 can comprise downloadable executable code that utilizes existing processing, memory, and data storage features of a device and/or the cloud.

As described above, the examination unit 104 can analyze data captured by one or multiple data acquiring devices and/or systems 102, for example, from one or multiple intra-oral data acquisition devices 102. The examination unit 104 can analyze data from one or multiple data acquisition devices 102 sequentially and/or simultaneously. The examination unit 104 can detect (and distinguish between) healthy and/or unhealthy conditions from the acquired data received, accessed, and/or processed (e.g., scans, radiographs, images, photographs, and/or video). The examination unit 104 can electronically quantify and map the oral cavity, dentition, and supporting hard and soft tissue structures. The examination unit 104 can use these quantifications and mappings to make diagnoses, predictions (e.g., prognoses), and treatment recommendations, as well as for designing treatment plans. For example, the processing unit 106 can identify, quantify, analyze and/or map existing conditions, predict the progression of existing conditions, provide a probability for the manifestation of currently non-manifested conditions, provide a recommendation to treat and/or monitor existing conditions, provide a recommendation to treat and/or monitor not yet manifested conditions (e.g., with preventative treatment), identify variables that are contributing to and causing the development of existing and/or not yet manifested conditions, identify educational protocols that can influence and succeed in changing patient behavior that is causing or is detrimental to dental health or its improvement, identify educational protocols most likely to influence and succeed in changing behavior that is causing or is detrimental to dental health or its improvement specific to the patient, for example, based partly or completely on physiologic, genetic, bacterial, and environmental factors, as well as their health history, or any combination thereof.

Using the processing unit 106, the examination unit 104 can quantify (e.g., measure), map (e.g., model), diagnose, and/or define the extent of dental deficiencies (e.g., functional deficiencies) as well as any other detectable (e.g., scannable, radiographable, photographable) dental conditions. While acquired data can provide a snapshot of the present, the processing unit 106 can "examine" (i.e., analyze) the acquired data to build a "picture" of past and future states with predictive and speculative modeling techniques such as statistical analysis involving comparisons to the norm and other data sets in which the past, present, and/or future states are already known (e.g., from other patients having conditions in the same or different stages and/or having interrelated causes to those conditions being treated or monitored in patient 101). This picture can come in the form of visual and/or numerical mappings as described in more detail below.

The statistical analysis can involve computing one or more statistical parameters, for example, maximums, minimums, medians, averages, norms, standard deviations, or any combination thereof. The statistical analysis can involve generating one or more statistical distributions, for example, discrete probability distributions and/or continuous probability distributions (e.g., normal/Gaussian distributions). The quantifications and mappings can be analyzed to determine one or more statistical parameters and/or to generate one or more statistical distributions. The quantifications and mappings can be statistical parameters and/or distributions. For example, the reference points determined from the data acquisitions can be statistical parameters and/or distributions.

The system 100 (e.g., the examination unit 104) can measure or compute one or more quantities associated with the acquired data, for example, dimensions, quantities associated with qualitative (e.g., color) characterizations, and statistical parameters. For example, the system 100 (e.g., the examination unit 104) can measure or compute one or more quantities representative of or associated with one or more anatomical markers and/or patterns (e.g., exact and/or estimated peaks, valleys, geometries, shapes, lines, perimeters, outlines, or any combination thereof), the relative positions of anatomical markers and/or patterns (e.g., the distances between them, their sizes), the relative positions of dental conditions (e.g., the distances between them, their sizes), the relative positions of hard and soft tissues (e.g., the distances between them, their sizes), light absorption, light reflection, colors (e.g., hues), tints, tones, and shades of colors (e.g., light, medium, and/or dark shades of a hue), changes in any of the foregoing, or any combination thereof.

The system 100 (e.g., the examination unit 104) can generate visual mappings (e.g., using one-, two-, three-, and/or four-dimensional representations) and/or numeric mappings (e.g., using numbers, ratios, and/or matrices) of the acquired data, for example, one or more of the dental conditions digitally represented by the acquired data. The visual and/or numeric mappings can include healthy, diseased, and/or deficient structures and tissues. The system 100 can generate or can produce and send instructions to generate one or more one-, two-, three-, and/or four-dimensional representations of acquired data (e.g., a scan, a radiograph, a photograph). The three- and four-dimensional visualizations can be, for example, 3D printed structures and/or 3D computer renderings, with the four-dimensional printed structures and/or renderings including time and/or date indicators thereon. The mappings can be used to create historical, current, and/or predictive models for the conditions digitally captured by the data acquisition device 102 and/or of healthy structures not associated with a condition. The mappings can be statistical distributions.

Quantifying and/or mapping the oral cavity and masticatory system can involve determining one or more reference parameters or regions (collectively referred to throughout as reference points). Each reference point can be quantitative or qualitative. Each reference point can be a numerical representation and/or a visual representation of a dental condition. For example, the reference points can correspond to one or more reference locations, reference contacts, reference contact regions, reference contact points, reference contact surfaces (e.g., reference occlusal surfaces), reference measurements, reference shapes, reference ratios, reference colors, shades, or tints, reference blood perfusion, or any combination thereof. The reference contacts and reference contact regions/points/surfaces identified by the system 100 can be on a single tooth or can be the areas of engagement between two teeth (e.g., a maxillary tooth and a mandibular tooth). The reference points can correspond to soft tissue having certain characteristics and/or hard tissue having certain characteristics. Such certain characteristics can include, for example, the size, shape, quantity (e.g., mass, volume, etc.), coloration, level of vascular perfusion, structure, structural integrity, or any combination thereof, of soft and/or hard tissue. For example, the reference points can correspond to one or more anatomical markers and/or patterns (e.g., exact and/or estimated peaks, valleys, geometries, shapes, lines, perimeters, outlines, contacts, contact regions/points/surfaces, or any combination thereof), the relative positions of soft and/or hard tissues relative to one another (e.g., the relative positions of one or more anatomical markers to one or more other of the same or different anatomical markers), light absorption, light reflection, colors (e.g., hues), tints, tones, and shades of colors (e.g., light, medium, and/or dark shades of a hue), changes in any of the foregoing, or any combination thereof. For example, the examination unit 104 can differentiate between—and can measure, map, or otherwise determine the extent of—plaque, enamel, dentin, pulp, gum, cement, nerves (e.g., innervation), blood vessels, bone, restorative materials, bacteria, or any combination thereof. The reference point identified by the system 100 can be exposed dentin, for example an exposed spot or area of dentin. As another example, the examination unit 104 can differentiate between the crown, neck, and/or root of each tooth, and can measure, map, or otherwise determine the extent of each. The reference point identified by the system 100 can be a ditch around the cervical margin. The distance between reference points can be determined by comparing a first and a subsequent reference point, for example using photogrammetry techniques. The reference points can be the quantifications and mappings described herein. The reference points can be separate from the quantifications and mappings described herein. The reference points can be derived (e.g., via the examination unit 104) from the quantifications and mappings described herein. To determine the reference points, the system 100 can determine one or more potential reference points, for example, by determining a potential subsequent (e.g., maximum) extent of the of the reference point.

The reference points can be independent from one another, for example, such that each reference point can be separately displayed or communicated to a user. The reference points can be layered (e.g., simultaneously displayed or communicated to a user). For example, one or more reference measurements can be displayed on a 2D visual representation of the dentition having colors indicative of where each dental condition is located. Each type of a dental condition can be associated with a different color, shade, tint, or hash markings.

The reference points of two different data acquisitions (e.g., a first data acquisition and a subsequent data acquisition) can be compared with one another to determine the progression of the identified conditions, including more than two data acquisitions (e.g., 3 to 50 data acquisitions, or more narrowly, 3 to 20 data acquisitions, or more narrowly still, 3 to 10 data acquisitions, or even more narrowly, 3 to 5 data acquisitions). This advantageously enables electronic tracking and observation of the dentition, the support structures and surrounding tissues, and the conditions, diseases, and/or conditions thereof.

The reference points can be a reference region that includes only the area or condition of interest (e.g., a contact area, exposed dentin, wear surface, or any combination), or a region slightly beyond the area or condition of interest. For example, a two-dimensional shape (e.g., a circle, an ellipse, a hemisphere, a triangle, square, rectangle, pentagon, hexagon, or other polygonal shape, including a series of connected line segments forming a closed shape, where the line segments can be straight and/or form one or more arcs), or a three-dimensional shape (e.g., sphere, spheroid, hemispheroid, ellipsoid, or three-, four-, five, six-, seven-, or more-sided prism) can extend around (e.g., around a center, a first end, a second end) of the area/condition of interest in a cross-sectional view and a three-dimensional view, respectively. The two- or three-dimensional shape can include the area/condition of interest and an area beyond that area. For example, the shape can extend at a constant or variable distance beyond a boundary of the contact area, for example, from about 0.1 mm to about 5.0 mm, including every 0.1 mm increment therebetween. Using a two-dimensional shape to surround the area or condition of interest in a side or cross-sectional view and/or a three-dimensional shape to surround the area or condition of interest in a three-dimensional view allows the reference point to be approximated.

Quantifying and/or mapping the oral cavity and masticatory system can involve determining one or more potential reference parameters or regions (collectively referred to throughout as potential reference points). The potential reference points can be smaller or larger than the first and second reference points. The system 100 can estimate one or more potential reference points, for example, based on one or more determined reference points, and/or based one or more other aspects of data acquired by the data acquisition device 102. The system 100 can determine one or more potential reference points from an analysis of data acquisition data, from which the system 100 can determine one or more corresponding actual reference points (simply referred to throughout as "reference points"). The actual reference points can be sized so that the corresponding potential reference points do not change (e.g., in size, in shape) between two adjacent data acquisitions. The potential reference points can provide the system 100 with a reference from which to anchor an analysis of a subsequent data acquisition, for example for calibration. The potential reference points can have any two-dimensional or three-dimensional shape as described above with respect to the reference points. The potential reference points can have the same or a different shape than the actual reference points. The reference and potential reference points can each have the same shape as or a different shape than another reference or potential reference point. The system 100 can determine a potential reference point for every reference point that is determined.

The system 100 (e.g., the examination unit 104) can predict the manifestation of not yet manifested conditions, for example, based partly or completely on physiologic, genetic, environmental, and/or bacterial factors, as well as their health history. The system can predict dental conditions, diseases, and deficiencies, for example, those described herein.

For example, to make predictions regarding when a not yet manifested condition will likely manifest, for example, with physical symptoms, the processing unit 106 can evaluate the variables identified as contributing to the identified existing conditions. The processing unit 106 can then determine the likelihood that a non-manifested condition that relates to or is associated with one or more of those variables will manifest in the future as an observable or otherwise detectable condition (e.g., within about 1-12 months or more, sometime within the next 1 year, 2 years, 3 years, 4 years, 5 years, 10 years, 15 years, or 20 or more years). Alternatively, or in combination, the processing unit 106 can evaluate other factors such as age and diet to predict the likelihood of a currently that a non-manifested condition will become observable in the future and/or predict the speed of its subsequent progression after becoming observable. The processing unit 106 can estimate the expected extent and/or location of the not yet manifested condition when it becomes observable, for example, by making one more or more underlying assumptions regarding a patient's physiology and/or behavior, the environment, and/or current treatment (e.g., no change, a small, moderate, and/or large change in current physiology, behavior, and/or environment, in addition to the success or failure rate of current treatments, if any, the projected treatment progression of either success, failure, and/or no change, and/or recorded or otherwise observed progression of the current treatment).

The system 100 (e.g., the examination unit 104) can diagnose dental conditions, diseases, and deficiencies, for example, those described herein.

The system 100 (e.g., the examination unit 104) can determine whether to treat or monitor one or more detected conditions, and/or can recommend a course of action to that effect. For example, the system 100 can generate a treatment recommendation whenever a diagnosis value is greater than or equal to a treatment threshold, and can generate a monitor recommendation whenever a diagnosis value is less than the treatment threshold. The treatment threshold can be tied to benchmark value that is applicable across patients, or the treatment threshold can be specific to the patient. The treatment threshold can correspond to a percentage deterioration (or estimation thereof) and/or a stage of the condition (or estimation thereof). For example, the system 100 can generate a treatment recommendation for percentage deteriorations of about 5% or more (where 0% corresponds to zero deterioration), 10% or more, 15% or more, or 20% or more. The system 100 can generate a treatment recommendation of conditions that are in a treatable stage.

The system 100 (e.g., the examination unit 104) can design educational protocols/plans that can influence and succeed in changing patient behavior that is causing or is detrimental to dental health or its improvement. For example, the system 100 can identify educational protocols most likely to influence and succeed in changing behavior that is causing or is detrimental to dental health or its improvement specific to the patient, for example, based partly or completely on physiologic, genetic, bacterial, and environmental factors, as well as their health history. The educational plans can include suggested reading material and video tutorials about the conditions a patient has and/or is at risk of having, a review schedule for the materials and tutorials, reminders regarding dental hygiene (e.g., brush teeth, floss, mouthwash, and the frequency of each), and cross-disciplinary collaboration recommendations and status tracking with, for example, health coaches, lifestyle coaches, and dieticians.

In this way, the examination unit 104 can perform structural, physiological, and/or functional analyses of existing conditions, for example, those identified by the processing unit 106, and then make diagnoses, predictions, and recommendations.

The electronic examination and documentation system 100 can electronically document or otherwise store examination and/or analysis results for use in baseline documentation, mapping (e.g., historical mapping, current mapping, and/or predictive mapping), statistical comparisons (e.g., comparisons to the norm), diagnosis, treatment planning, patient education, or any combination thereof. The electronically documented or otherwise stored data can be queried or otherwise retrieved during the evaluation and analysis of one or multiple subsequent data acquisitions (e.g., scans, x-rays, photographs) to be able to accurately determine the progression of previously examined conditions, for example, by comparing the results of a subsequent data acquisition to the results of one or more previous data acquisitions. The examination unit 104 can compare the results of a data acquisition (e.g., the initial data acquisition and/or one or more subsequent data acquisitions) to the results of one or more previously obtained data acquisitions from the same patient and/or from one or more different patients. For example, the storage can be useful for storing an initial baseline data acquisition and comparing data associated therewith (e.g., quantifications, mappings, reference points) to one or more subsequent data acquisitions (e.g., scans, radiographs, photographs), thereby enabling electronic tracking and observation of the dentition, the support structures and surrounding tissues, and the conditions, diseases, and/or conditions thereof.

The examination unit 104 can have and/or can build a library of patient-specific and non-patient specific examination and analysis data, for example, using memories 108 and 112. Such libraries of data can allow one-time data acquisitions and/or each subsequent data acquisition to be more informative to the patient, medical professional, and examination unit 104 alike. The electronically stored data can allow the system 100 to build dental narratives for one or multiple teeth that can be quickly referenced and provide critical details regarding a person's health that visual inspection of data acquisition results (e.g., scans, radiographs, photographs) would not provide alone. These stories are not only desirable for the dentist and/or the examination unit 104 to make diagnoses and/or prognoses (e.g., predictions/forecasts of the progression of existing conditions) and to better educate patients, they are also desirable because they give patients more freedom in selecting their dental care provider, as the initial ramp up period a new dentist must undergo when welcoming a new patient to their practice is reduced by making a patient's history more accessible, understandable, and readily digestible.

For example, the quantifications and mappings disclosed herein can allow dentists to more readily review a patient's dental health and history "at a glance"—a fully accurate and precise comprehensive glance—as opposed to the more laborious method of pouring over old paper records, reviewing lengthy digital records comprising rushed or incomplete dentist/medical notes, or visually reassessing an endless collage of raw acquired data in which a new set of eyes must confirm or re-confirm past work. The examination unit 104 can focus a dentist's attention on what's important, for example, by assigning different weights to different conditions, for example, based on the type, severity (e.g., extent), and/or stage of the condition. Such weights can correspond to different sections in the electronic dental data (e.g., electronic medical record) that the examination unit 104 can store, different text colors in the electronic dental record, different indicators on the one or more of the generated mappings and quantifications such as colors, symbols, magnified views, colored shapes (e.g., a red rectangle around important conditions and/or quantifications) and the like, as well as different indicators associated with the one or more generated mappings and quantifications such audible warnings or messages that are emitted, for example, automatically when that condition is being viewed or manually when a user clicks on the display 114 or touches the screen 114 to "play" the warning or message. The system 100 can therefore make dentists more efficient, patients more knowledgeable and dental treatments more successful and fulfilling. This improved efficiency that the system 100 provides can in turn encourage patients to find those care providers who they are most comfortable with, or otherwise empower them to be more inclined to leave those care providers the patient may be unhappy with for one reason or another, as it reduces the amount of non-transferrable information that is lost when a patient switches from dentist to another. For the same reasons, the system 100 makes finding a new dentist, for example, due to geographic relocations (e.g., due to work) less distressing for the patient.

The examination unit 104 can use acquired data and processed data (e.g., acquired data that has been processed) to create artificial intelligence and/or machine learning with respect to dental structural and tissue changes over time, for example, by using and/or creating one or more databases of acquired data and/or processed data, such as those described above. For example, the processing unit 106 can be programmed with an algorithm and/or a cloud computing system (e.g., one or more servers and/or networks) can be used to digest all the collected data at the time of baseline exams and at follow-up data acquisitions (e.g., follow-up intraoral digital data acquisitions, such as follow-up scans, x-rays, photographs). The data collected can be processed and compared with one or more libraries of data (e.g., databases) that are patient-specific (i.e., data of only a single patient 101) and/or non-patient specific (i.e., data of one or multiple people different from patient 101 and/or of multiple people including patient 101) to more accurately determine the progress of the disease, make diagnoses and predictions, and to compare functional dental deficiencies against the norm. In this way, artificial intelligence and machine learning can desirably allow dentists and patients alike to make more informed decisions about the dental treatment based on the more accurate diagnoses.

One or more aspects of the system 100 can be voice and/or gesture controlled. For example, the examination unit 104 can be voice and/or gesture controlled via a control interface. Alternatively, or in combination, the system 100 can have a control interface such that the examination unit 104 can be instructed to "look for"—identify, if it exists—one or more specific conditions, as opposed to performing a fully comprehensive examination of the data acquisition results. This can be useful, for example, where time is limited, to re-confirm the existence of an identified condition, and/or to re-confirm the absence of a condition. It also gives medical professionals the ability to focus subsequent exams on areas that the examination unit 104 may not have emphasized in previous or current analyses. Such a control unit can receive input to analyze the entire dentition, a subset thereof, a single tooth, a portion of a single tooth, one or more portions of multiple teeth, or any combination thereof. The control unit can be, for example, a controllable interface, including one or more controls (e.g., one or more multi-state controls), that can be manually or automatically manipulated to adjust the analysis parameters of the system 100. The analysis parameters can be set, for example, to identify one or multiple conditions, one or multiple reference points (should they exist), soft tissue having a certain characteristic, hard tissue having a certain characteristic, or any combination thereof. Such certain characteristics can include, for example, the size, shape, quantity (e.g., mass, volume, etc.), coloration, level of vascular perfusion, structure, structural integrity, or any combination thereof, of soft and/or hard tissue. The controls can be one or more touch screens, touch surfaces, or manipulatable mechanisms (e.g., buttons, switches, knobs, or combinations thereof). The manipulatable mechanisms can be translatable and/or rotatable.

As described above, the examination unit 104 can quantify and/or map any detectable (e.g., scannable, radiographable, photographable) dental condition. Such conditions can include dental structures, diseases, and deficiencies (e.g., functional deficiencies). To allow for such analysis, the examination unit 104 can determine the location and condition of soft and/or hard tissue, including its size, shape, quantity (e.g., mass, volume, etc.), coloration, level of vascular perfusion, structure, structural integrity, or any combination thereof. For example, the examination unit 104 can differentiate between—and can measure, map, or otherwise determine the extent of—plaque, enamel, dentin, pulp, gum, cement, nerves (e.g., innervation), blood vessels, bone, restorative materials, bacteria, or any combination thereof. As another example, the examination unit 104 can differentiate between the crown, neck, and/or root of each tooth, and can measure, map, or otherwise determine the extent of each. The examination unit 104 can identify the type of each tooth digitally captured (e.g., imaged via a scan, an x-ray, a photo, or any combination thereof), for example, whether the tooth is a molar, premolar, canine, or incisor. Based partly or completely on an analysis of some or all of the above, the examination unit 104 can diagnose the conditions a patient (e.g., patient 101) has, if any. The examination unit 104 can also identify healthy tissue and highlight this for discussion with the patient, or to directly inform the patient. The identification of healthy tissue in addition to unhealthy tissue can provide encouraging feedback to patients, and facilitate more active participation by the patient 101 in their own treatment.

The mappings (e.g., numeric and/or visual) can have multiple layers that are selectable and/or have varying degrees of transparency or other distinguishing features (e.g., colors, color gradients, symbols, etc.). For example, the enamel and dentin layer can be selected such that the unselected features or the other selectable features are not shown on the map. Every iteration of selectable features is hereby disclosed (i.e., anything that can be quantified and/or mapped), and is therefore claimable.

Acquirable (e.g., observable and/or detectable, for example, scannable, radiographable, photographable) and electronically examinable dental structures include, for example, attrition, abrasion, abfraction, erosion, wear, non-carious tooth substance loss, fractured teeth, fracture lines in teeth, anomalies, missing teeth, edentulous spaces, crowding and spacing of the dentition, restorations, defective restorations, restorative materials, caries, re-current caries, or any combination thereof. As described below, FIGS. 2A-10 illustrate various exemplary conditions that the system 100 can observe, detect, analyze, and electronically document, in any combination, along with exemplary reference points for each. The various properties of reference and potential reference points described in relation to each of FIGS. 2A-10 below are applicable for any reference and potential reference point for any dental disease, condition, or deficiency, for example for any of the other conditions shown in FIGS. 2A-10. For clarity in the following description, some properties have been repeated in the various Figure descriptions, and some have not. However, and merely to reiterate the intent of the following description of FIGS. 2A-10, the inclusion of subject matter in the descriptions of some figures but its omission from other figures is not an omission of that subject matter from those figures that do not include such descriptions.

Attrition

Figures 2A, 2B, 2C, 2D, 2E:
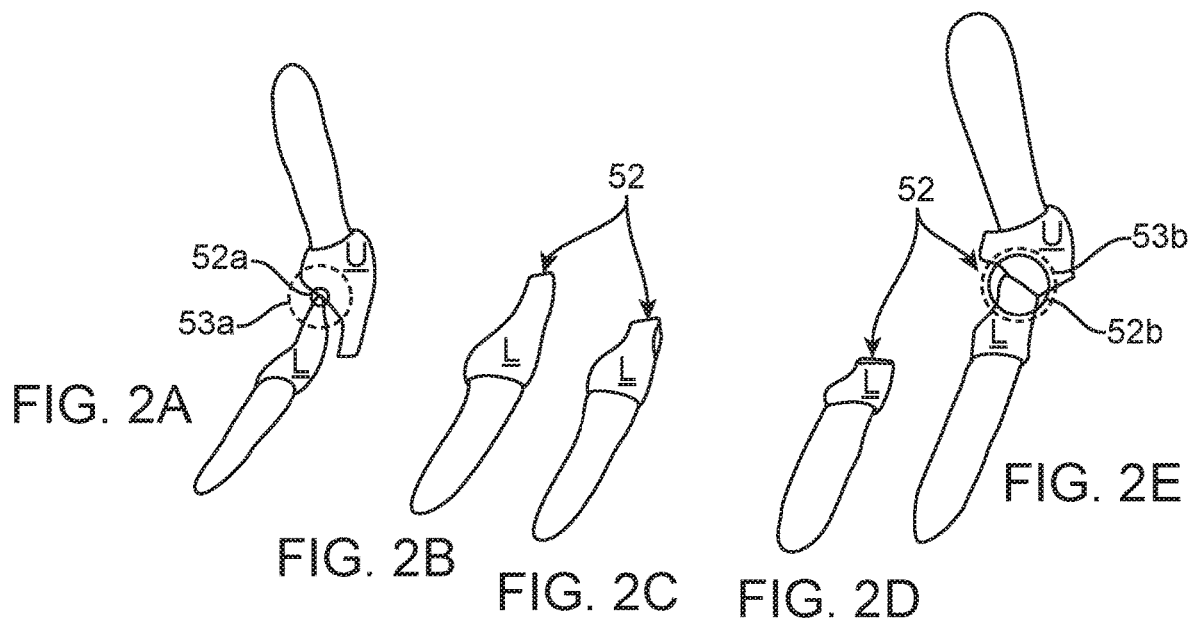
FIGS. 2A-2E illustrate a diagrammatic representation of a variation of dental attrition formation.

Attrition is the loss of tooth substance caused by physiologic tooth-to-tooth contact. Attrition predominately causes wear on the incisal edges and occlusal surfaces of the teeth. One or more 2D or 3D images (e.g., scans, x-rays, photographs) can be used to identify or form an image of attrition. 2D images can be constructed into a 3D image or a 3D image can be generated directly, for example using a camera, an x-ray device, or an intra-oral 3D scanner. FIGS. 2A-2E illustrate a diagrammatic representation of a variation of dental attrition 52 forming over time. FIG. 2A illustrates an upper tooth U and a lower tooth L before the effects of attrition can be seen, FIG. 2E illustrates attrition 52 on the upper and lower teeth U, L, and FIGS. 2B-2D illustrate the progression of the attrition 52 on the lower tooth L in the span of time between the snapshots shown in FIGS. 2A and 2E.

The reference point for attrition can be the contact point or contact surface (e.g., planar, curved, or irregularly shaped) where two or more teeth contact one another, for example, where two occlusal surfaces contact each other, and/or where an occlusal surface of a first tooth contacts a side of a second tooth. The reference point for attrition can be exposed dentin, for example, an exposed spot or area of dentin. For example, FIGS. 2A and 2E illustrate that the system 100 can determine a first reference point 52a and a second reference point 52b between the upper and lower teeth U, L. The system 100 can determine the first reference point 52a from a first (e.g., baseline) data acquisition, and the second reference point 52b from a subsequent (e.g., second, third, fourth, fifth, or more) data acquisition. The system 100 can determine the dimensions and the extent of the first and second reference points 52a, 52b and compare them to each other. For example, the length, width, and height, as well as the size, surface area, and outline of each reference point (e.g., 52a and 52b), in any combination, can be determined and compared to one another. The volume of tooth loss between any two reference points (e.g., 52a and 52b) can be determined and compared, as can a ratio between any measured dimension or derived value (e.g., surface area). The area of the surfaces that are undergoing wear can be measured and quantified. The area of dentin exposed can be measured and quantified.

The first and second reference points 52a, 52b (also referred to as reference regions) can correspond to where contact between the upper and lower teeth U, L occurs (e.g., the one or more points or regions where it actually occurs, and/or a boundary extending around the outermost contact points and/or regions). The first and second reference points 52a, 52b can correspond to where dentin has been exposed. Alternatively or additionally, the first and second reference points 52a, 52b can be a reference region that includes the contact area and a region slightly beyond the contact area. For example, a two-dimensional shape (e.g., a circle, an ellipse, a triangle, square, rectangle, pentagon, hexagon, or other polygonal shape, including a series of connected line segments forming a closed shape, where the line segments can be straight and/or form one or more arcs) or a three-dimensional shape (e.g., sphere, spheroid, ellipsoid, or three-, four-, five, six-, seven-, or more-sided prism) can extend around a center of the contact area in a cross-sectional view and a three-dimensional view, respectively. The two- or three-dimensional shape can include the contact point and an area beyond the contact area. For example, the shape can extend at a constant or variable distance beyond a boundary of the contact area, for example, from about 0.1 mm to about 5.0 mm and every 0.1 mm increment therebetween. Using a two-dimensional shape to surround the contact area in a side or cross-sectional view and/or a three-dimensional shape to surround the contact area in a three-dimensional view allows the reference point to be approximated. For example, FIGS. 2A and 2E illustrate that the first and second circles 52a, 52b each surround the contact area and include a space around the contact area. The area or volume of the first and second reference shapes (e.g., first and second reference circles 52a, 52b) can be compared to one another so that the extent of tooth loss due to abrasion can be approximated. Although only a single side view reference point is illustrated in FIGS. 2A and 2B, the system 100 can determine multiple two-dimensional side or cross-sectional reference points, and/or can determine one or multiple three-dimensional reference points.

FIGS. 2A and 2E also illustrate that the system 100 can determine a first potential reference point 53a and a second potential reference point 53b. The first and second potential reference points 53a, 53b can be smaller or larger than the first and second reference points 52a, 52b. For example, FIGS. 2A and 2E illustrate that the first and second potential reference points 53a, 53b can be larger than the first and second reference points 52a, 52b. The system 100 can estimate the first and second potential reference points 53a, 53b, for example, based on the first and second reference points 52a, 52b. The first and second reference points 53a, 53b, can be sized so that the first and second potential reference points 53a, 53b do not change between two adjacent data acquisitions. The first and second potential reference points 53a, 53b can provide the system 100 with a reference from which to anchor an analysis of a subsequent data acquisition. The first and second potential reference points 53a, 53b can have any two-dimensional or three-dimensional shape as described above with respect to the first and second reference points 52a, 52b. The first and second potential reference points 53a, 53b can have the same or a different shape than the first and second reference points 52a, 52b. The reference and potential reference points can each have the same shape as or a different shape than another reference or potential reference point. The system 100 can determine a potential reference point for every reference point that is determined.

Although not illustrated in FIGS. 2A and 2E, the reference and potential reference points 52a, 52b, 53a, 53b can enclose or surround dentin that has been exposed due to wear.

Tooth Wear & Non-Carious Tooth Substance Loss

Figure 3:
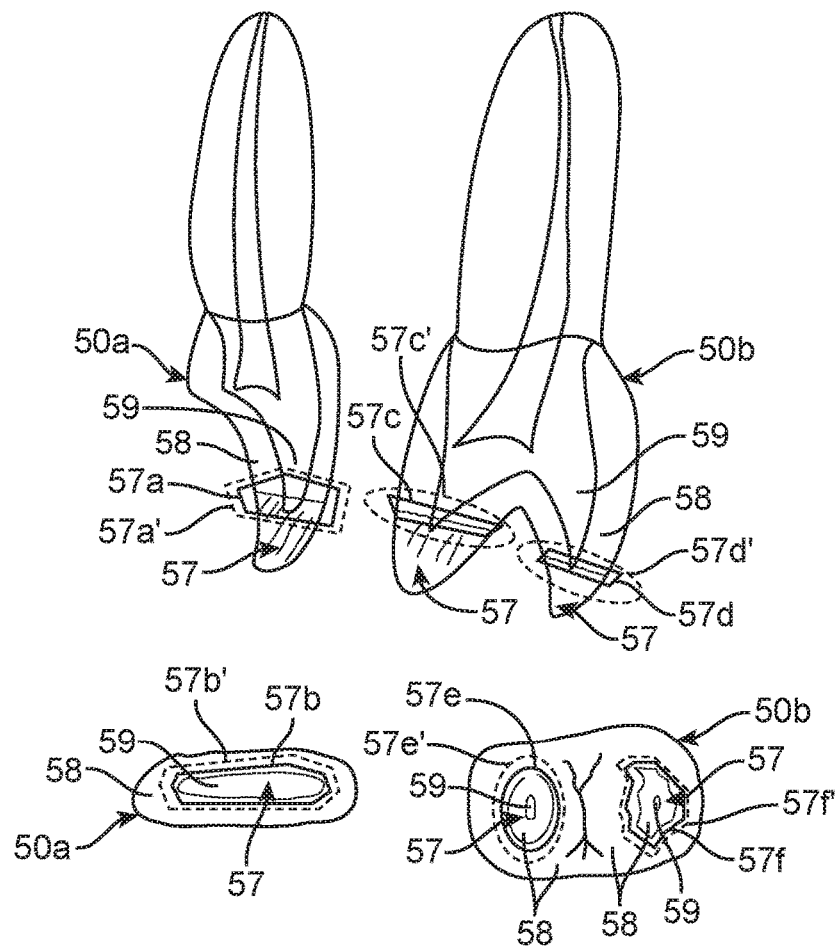
FIG. 3 illustrates a diagrammatic representation of a variation of abfraction and/or abrasion at the cervical margin of a tooth.

Tooth wear and non-carious tooth substance loss refers to the loss of tooth substance by means other than dental caries or trauma. One or more 2D or 3D images (e.g., scans, x-rays, photographs) can be used to identify or form an image of attrition. 2D images can be constructed into a 3D image or a 3D image can be generated directly, for example using a camera, an x-ray device, or an intra-oral 3D scanner. FIG. 3 illustrates a diagrammatic representation of two cross-sectional and occlusal views of a variation of a first and a second tooth 50a, 50b with wear 57 extending into the enamel 58 and dentin 59. A portion of the dentin 59 is shown exposed on the occlusal surfaces.

The reference point for tooth wear and non-carious tooth substance loss can be the contact point or contact surface where two or more teeth contact one another, for example, where two occlusal surfaces contact each other, or where an occlusal surface of a first tooth contacts a side of a second tooth. The reference point for tooth wear and non-carious tooth substance loss can be exposed dentin, for example, an exposed surface of dentin. For example, FIG. 3 illustrates that the system 100 can determine a first side view reference point 57a and a first occlusal view reference point 57b for the first tooth 50a, and can determine first and second side view reference points 57c, 57d and first and second occlusal view reference points 57e, 57f for the second tooth 50b. The system 100 can determine the various reference points 57a-57f on the first and second teeth 50a, 50b from a first data acquisition (e.g., a baseline or subsequent data acquisition). The system 100 can determine the dimensions and the extent of the various reference points 57a-57f on the first and second teeth 50a, 50b and compare them to subsequent reference points determined from one or more subsequent data acquisitions. For example, the length, width, and height, as well as the size, surface area, and outline of each reference point (e.g., 57a-57f), in any combination, can be determined and compared to one another. The volume of tooth loss between the determined reference points (e.g., 57a-57f) and reference points determined from a subsequent data acquisition can be determined and compared, as can a ratio between any measured dimension or derived value (e.g., surface area). The area of the surface that is undergoing wear can be measured and quantified. The area of dentin exposed can be measured and quantified.

FIG. 3 illustrates that the system 100 can determine a reference point for each tooth individually. The various reference points 57a-57f can correspond to where the first and second teeth 50a, 50b contact another tooth (not shown). The various reference points 57a-57f can correspond to where dentin has been exposed. Alternatively or additionally, the various reference points 57a-57f can correspond to a boundary extending around the outermost contact points and/or regions, for example, such that the reference points 57a-57f comprise a reference region that includes a contact area and a region slightly beyond the contact area. The various reference points 57a-57f can have a two-dimensional and/or a three-dimensional shape as described above with reference to FIGS. 2A and 2E. For example, FIG. 3 illustrates that the various reference points 57a-57f can each have an irregular polygonal shape, and/or a non-angular shape (e.g., circular shape, elliptical shape, hemispherical). Although not shown, the area or volume of the various reference points 57a-57f (e.g., the various reference shapes 57a-570 can be compared to one another so that the extent of tooth loss due to abrasion can be approximated. Although only a single side and occlusal view reference point is illustrated for each of the first and second teeth 50a, 50b in FIG. 3 for each area of abrasion shown, the system 100 can determine multiple two-dimensional side or cross-sectional reference points, and/or can determine one or multiple three-dimensional reference points.

FIG. 3 also illustrates that the system 100 can determine a first side view potential reference point 57a' and a first occlusal view potential reference point 57b' for the first tooth 50a, and can determine first and second side view potential reference points 57c', 57d' and first and second occlusal view potential reference points 57e', 57f' for the second tooth 50b. The potential reference points illustrated in FIG. 3 can have the same properties as the potential reference points described above with reference to FIGS. 2A and 2E.

Although not illustrated in FIG. 3, the reference and potential reference points 57a-57f and 57a'-57f' can enclose or surround dentin that has been exposed due to wear.

Erosion

Figure 4:
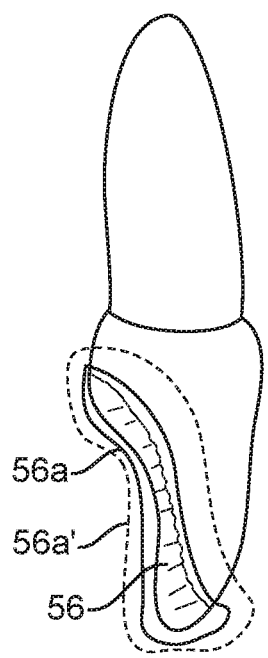
FIG. 4 illustrates a diagrammatic representation of a variation of chemical erosion of a tooth.

Erosion is the chemical dissolution of tooth substance caused by acids unrelated to the acids produced by bacteria in dental plaque. Erosion can occur with excessive consumption of acidic foods and drinks, or medical conditions involving the repeated regurgitation and reflux of gastric acid. Erosion on a tooth can present as one or more discolored regions that have a different shade as compared to non-eroded portions of the tooth/teeth. For example, the eroded portion of a tooth can be grey, including light grey to dark grey. Erosion can be captured using a scanner, for example a computed tomography (CT) scanner (e.g., a CBCT scanner). FIG. 4 illustrates a diagrammatic representation of a variation of chemical erosion 56 of a tooth. FIG. 4 illustrates that the system 100 can identify or otherwise determine a reference point 56a and a potential reference point 56a'. The system 100 can determine the reference and potential reference points 56a, 56a' based on the color (e.g., shade) of one or more portions of the tooth. For example, the shade of the reference regions 56a, 56a' can include a shade of color that is darker (or lighter) than the portion of the tooth not included in the reference regions 56a, 56a'. The area of erosion can be the darker and/or lighter portions of the teeth. FIG. 4 further illustrates that the reference points (e.g., reference points 56a, 56a') can have an irregular curved shape comprised one or more curved line segments. The system 100 can use a shade detection device (e.g., an electronic tooth shading ruler, a camera) to calibrate the detected shades so that the detected shades can be compared to one another over time, for example from different a first and a subsequent data acquisition.

Abrasion & Abfraction

Figure 5:
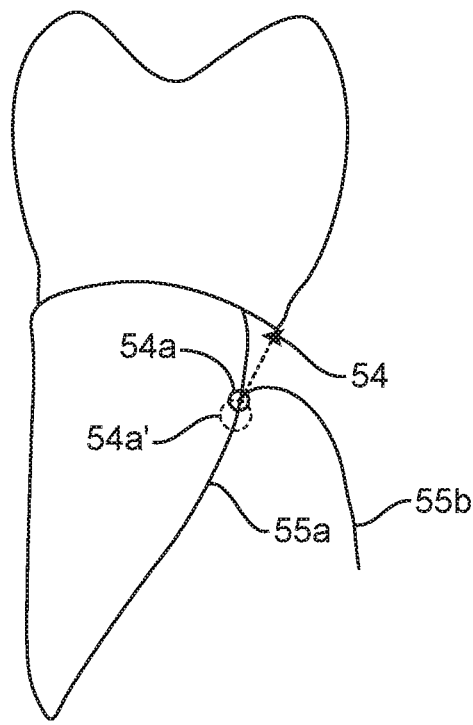
FIG. 5 illustrates a diagrammatic representation of two variations of teeth with wear.

Abrasion is the loss of tooth substance caused by physical means other than teeth (i.e., other than by physiologic tooth-to-tooth contact). Abrasion tends to present as rounded ditching around the cervical margins of teeth, commonly described as shallow, concave or wedge shaped notches. Abrasion can be caused by improper use of a toothbrush, dental floss or toothpicks. Abfraction is similar to abrasion but is caused by bruxing (i.e., grinding) or clenching of the teeth. Bruxing/clenching causes enough stress at the cervical margin to create wedge shaped deficits. One or more 2D or 3D images (e.g., scans, x-rays, photographs) can be used to identify or form an image of abrasion and abfraction. 2D images can be constructed into a 3D image or a 3D image can be generated directly, for example using a camera, an x-ray device, or an intra-oral 3D scanner. The gum attachment point 54a to the tooth 55a can be captured using a scanner, for example a computed tomography (CT) scanner (e.g., a CBCT scanner). The images of a CBCT scanner and a radiograph can be combined to quantify and/or map abrasion and abfraction where the gum attachment point to a tooth is being tracked. FIG. 5 illustrates a diagrammatic representation of a variation of abfraction and/or abrasion 54 at the cervical margin of a tooth. FIG. 5 illustrates where the gum 55a contacts the tooth 55b.

The reference point for abrasion and abfraction can be the contact point or contact surface where two or more teeth contact one another, for example, where two occlusal surfaces contact each other, or where an occlusal surface of a first tooth contacts a side of a second tooth. The reference point for abrasion and abfraction can be a surface notch, ditch, divot, or indentation on a tooth surface, for example, on a side of the tooth, on an occlusal surface, and/or on the ridge marking the boundary between a side tooth surface and an occlusal surface. The reference point for abrasion and abfraction can be exposed dentin, for example, an exposed surface of dentin. The reference point for abrasion and abfraction can be the contact point between the gum and a tooth.

For example, FIG. 5 illustrates that the system 100 can determine a first reference point 54a and a first potential reference point 54a'. The reference points 54a and 54a' can be a gum-tooth contact location (i.e., potential contact locations for the potential reference point 54a'), and can correspond to a lower (or upper) extent of a rounded ditching around a cervical margin of a lower tooth (or upper tooth). FIG. 5 further illustrates that the reference and potential reference points (e.g., reference points 54a and 54a') do not need to be concentric with one another. FIG. 5 further illustrates that the boundary of a potential reference point can overlap with a center of a the actual reference point, for example for the possible observable event in which the gum contact point remains at the same location in a subsequent data acquisition, and does not further deteriorate (by moving downward on the page of FIG. 5 along the tooth surface), and does not improve (by moving upward on the page of FIG. 5 along the tooth surface).

Fractures & Fracture Lines

Figure 6:
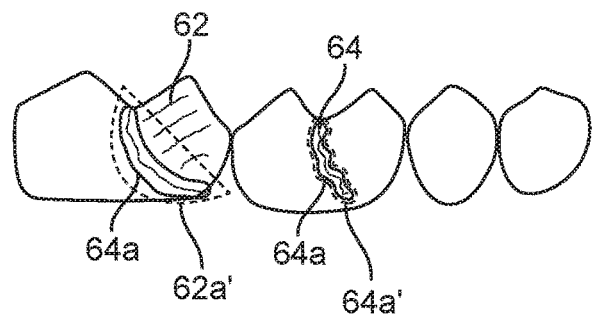
FIG. 6 illustrates a diagrammatic representation of a variation of fractured teeth and fracture lines.

Fractured teeth are missing part of if not all the clinical crown of the tooth below or above the gum line. Fracture surfaces can present as one or more discolored regions, and can change the boundary of teeth to a boundary outside of physiological norms. Fracture lines are within intact teeth/ tooth structures and indicate that the tooth/teeth are weakening. Fracture lines generally cannot be visually monitored over time using traditional manual visual inspection and examination methods. Fracture lines can present as one or more discolored regions or lines that have a different shade as compared to non-fractured portions of the tooth/teeth. For example, a fracture line of a tooth can be grey, including light grey to dark grey. Fractures (e.g., fracture surfaces) and fracture lines can be captured using a camera and/or an x-ray device, as well as a color detection device as described above with reference to FIG. 4. For example, the system 100 can use a shade detection device (e.g., an electronic tooth shading ruler, a camera) to calibrate the detected shades so that the detected shades can be compared to one another over time, for example from different a first and a subsequent data acquisition. FIG. 6 illustrates a diagrammatic representation of a variation of a fractured tooth having a fractured portion 62 that has broken away from the tooth and a variation of a tooth having a fracture line 64. FIG. 6 illustrates that the system 100 can identify or otherwise determine a reference point 62a and a potential reference point 62a' corresponding to a fracture surface, and can identify or otherwise determine a reference point 64a and a potential reference point 64a' corresponding to a fracture line. The system 100 can determine the reference and potential reference points 62a, 62a', 64a, 64a' based on the color (e.g., shade) of one or more portions of the tooth. For example, the shade of the reference regions 62a, 62a', 64a, 64a' can include a shade of color that is darker (or lighter) than the portion of the tooth not included in the reference regions 62a, 62a', 64a, 64a'. The fracture surface and fracture line can be the darker and/or lighter portions of the teeth.

Tooth Anomalies

Figure 7:
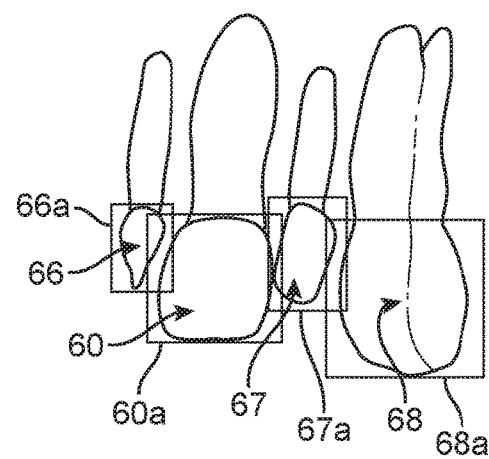
FIG. 7 illustrates a diagrammatic representation of a variation of microdontia, supernumerary teeth and fusion of teeth.

Anomalies of the teeth can include, for example, supernumerary teeth, hyperdontia, hypodontia, fusion, germination, macrodontia, microdontia, or any combination thereof. FIG. 7 illustrates a diagrammatic representation of a normal sized tooth 60, microdontia 66, supernumerary teeth 67 and a fusion of teeth 68. One or more 2D or 3D images (e.g., scans, x-rays, photographs) can be used to identify or form an image of such anomalies. 2D images can be constructed into a 3D image or a 3D image can be generated directly, for example using a camera, an x-ray device, or an intra-oral 3D scanner. The system 100 can determine the type of teeth (e.g., molar, premolar, canine, or incisor) imaged or otherwise under digital evaluation. The system 100 can identify or otherwise determine a reference point for each tooth, with each reference point corresponding to the size of the tooth, or a representative size of the tooth. For example, FIG. 7 illustrates that the system 100 can determine reference points 60a, 66a, 67a, and 68a for teeth 60, 66, 67 and 68, respectively.

The size of the reference points (e.g., 60a, 66a, 67a, and 68a) can be the actual size or an approximate size of a tooth. For example, FIG. 7 illustrates that the references points 60a, 66a, 67a, and 68a can be approximated with squares and rectangles; however, any curved or angular 2D shape (e.g., circles, ellipses, and polygons) or 3D shape (e.g., spheres, spheroids, ellipsoids, hemispheroids, and prisms) is appreciated. The reference points can be measured in any side view, occlusal view, 3D view, or can be construction of one or more views. For example, FIG. 7 illustrates that the references points 60a, 66a, 67a, and 68a can be side view reference points.

The size of each reference point can be the volume of the tooth, the total surface area of the tooth (e.g., above the gum line), the surface area of an occlusal surface of the tooth, the surface area of one or more sides of the tooth, the surface area of a portion of any of these measured surface areas, or any combination thereof. When multiple teeth are imaged, the same or different reference point measurement can be used on each tooth. Further, multiple reference point measurements can be performed on the same tooth and then averaged.

The reference points (e.g., 60a, 66a, 67a, and 68a) can be the surface area of one or more sides of each of the teeth 60, 66, 67 and 68, and/or the occlusal surface of each of the teeth 60, 66, 67 and 68. The surface area in the squares and rectangles 60a, 66a, 67a, and 68a can account for the curvature of the teeth within the squares and rectangles 60a, 66a, 67a, and 68a (e.g., at the corners of the teeth, and/or along the faces of the teeth), or the surface area in the squares or rectangles 60a, 66a, 67a, and 68a can ignore or not measure the surface area attributable to curvature of a tooth surface. Alternatively or additionally, the areas of the squares and rectangles 60a, 66a, 67a, and 68a can be used to approximate the size of the teeth. Although not shown, the geometric shape positioned over the teeth (e.g., the squares and rectangles 60a, 66a, 67a, and 68a) can be selected such that the tooth is entirely within the geometric shape, and such that each side of the geometric shape has a location that is 1 mm or closer to a surface of the tooth.

The system 100 can calibrate the sizes of the teeth against a database of sizes, for example by selecting one or more normal sized teeth and comparing the selected teeth to the teeth sizes in the database. The sizes in the database can be acquired from the teeth of other patients and/or can be theoretical teeth sizes, where teeth are compared to other like teeth, not other similar teeth, such that each tooth in a dentition is compared to a tooth in the exact same position as measured in another patient or modeled in a theoretically sized dentition. The sizes in the database can be acquired from other similar teeth of the patient, other similar teeth of other patients and/or can be theoretical teeth sizes of other similar teeth, where "other similar teeth" means that molars are compared to molars, premolars are compared to premolars, canines are compared to canines, and incisors are compared to incisors, including either teeth in the same position or a different position. For example, the reference points 60a, 66a, 67a, and 68a can be compared to the database sizes (i.e., sizes of other similar teeth of the patient, sizes of the same or one or more other similar teeth of one or more other patients, or theoretical sizes of the tooth or other similar teeth). Alternatively or additionally, the system 100 can have a database with a threshold size for each tooth. The system 100 can compare the reference points 60a, 66a, 67a, and 68a to the respective threshold sizes. By comparing reference points (e.g., reference points 60a, 66a, 67a, and 68a) to one or more database sizes and/or one or more reference thresholds, the system 100 can determine whether a dentition comprises supernumerary teeth, hyperdontia, hypodontia, fusion, germination, macrodontia, microdontia, or any combination thereof. For example, FIG. 7 illustrates that the system 100 can identify microdontia 66 where the reference point (e.g., 66a) has a size that is less than a database size and/or a threshold size. The system 100 can identify supernumerary teeth 67 where the reference point (e.g., 67a) has a size that is less than a database size and/or a threshold size. The system 100 can identify tooth fusion 68 where the reference point (e.g., 68a) has a size that is greater than a database size and/or a threshold size.

Missing Teeth & Edentulous Spaces

Figure 8:
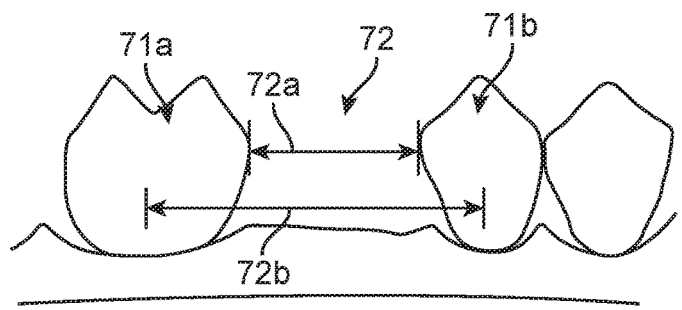
FIG. 8 illustrates a diagrammatic representation of a variation of a missing tooth and an edentulous space.

Missing teeth and edentulous spaces can affect masticatory efficiency and cause structural shifts and are therefore desirable to document. FIG. 8 illustrates a diagrammatic representation of a variation of a missing tooth and an edentulous space 72. One or more 2D or 3D images (e.g., scans, x-rays, photographs) can be used to identify or form an image missing teeth and edentulous spaces 72. 2D images can be constructed into a 3D image or a 3D image can be generated directly, for example using a camera, an x-ray device, or an intra-oral 3D scanner. A computed tomography (CT) scanner (e.g., a CBCT scanner) can be used to capture gaps between teeth. For example, a 3D intra-oral scanner and an x-ray device can be used to determine the presence of an edentulous space 72 where a baby tooth is under (e.g., still under) the gum.

FIG. 8 illustrates that the system 100 can determine the gap, if any, between adjacent teeth. For example, the system 100 can determine a reference point between adjacent teeth that corresponds to a gap, if any, between the adjacent teeth. For example, FIG. 8 illustrates that the system 100 can determine a first and/or a second reference point 72a, 72b, where each reference point can quantify the size of the gap (e.g., edentulous space) 72 between a first tooth and a second tooth (e.g., first and second teeth 71a, 71b). The first reference point 72a can be the size (e.g., length, width) of the gap 72 as measured from the two closest points of the first and second teeth 71a, 71b. The second reference point 72b can be the size (e.g., length, width) of the gap 72 as measured from the center, or an approximate center, of the first and second teeth 71a, 71b. The system 100 can compare the dimensions 71a and/or 71b to a threshold gap dimension, where the threshold gap dimension can be from about 1 mm to about 10 mm, including every 1 mm increment therebetween. The system 100 can indicate the presence of a gap (e.g., edentulous space) where the first and/or second dimensions 71a, 71b matches or exceeds the threshold gap dimension.

Restorations, Defective Restorations & Restorative Materials

Figures 9A, 9B:
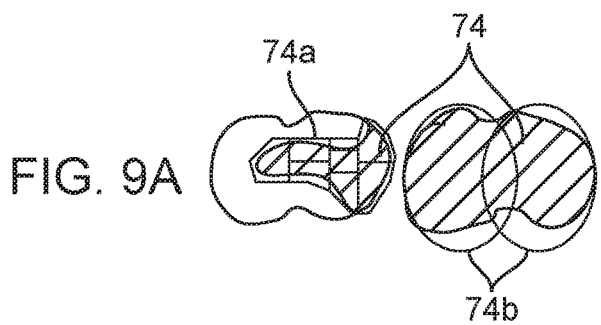
FIGS. 9A-9D illustrate diagrammatic representations of variations of different restorative materials for dental restorations, demineralization, decay and re-current decay.
Figures 9C, 9D:
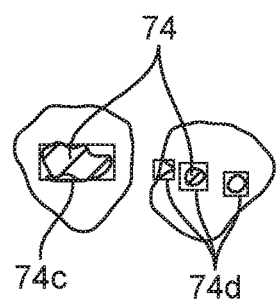

Restorations, defective restorations, and restorative materials are desirable to electronically document as well. Caries and re-current caries around existing dental restorations is the demineralization and bacterial invasion of the tooth structures. Restorations on a tooth can present as one or more discolored regions that have a different shade as compared to non-eroded portions of the tooth/teeth. For example, the restored portion of a tooth can be grey, including light grey to dark grey when digitally acquired, for example with an x-ray device or a scanner (e.g., a computed tomography (CT) scanner or cone beam CT (CBCT) scanner). FIGS. 9A-9D illustrate diagrammatic representations of variations of different restorative materials 74 for dental restorations, demineralization, decay and re-current decay. FIGS. 9A-9D illustrate that the system 100 can identify or otherwise determine reference points 74a, 74b, 74c, and 74d that can be tracked over time in one or more subsequent data acquisitions after an initial data acquisition, for example to determine the occurrence and extent of demineralization, decay and re-current decay. Using such imaging techniques, the system 100 can identify the discoloration caused by restorative material, including restorative material made of a material that has the same color as teeth when viewed by the naked eye, but a different color when captured by an x-ray device or CT (e.g., CBCT) scanner. FIG. 9A further illustrates that the reference and potential reference points disclosed herein can be separated into one or more sub-regions, for example, 8 sub-regions as shown for reference point 74a. FIG. 9B further illustrates that the reference and potential reference points disclosed herein can have one or more overlapping regions, for example, 1 overlapping region as shown for reference point 74b. FIG. 9D further illustrates that multiple reference and potential reference points can be identified on a single tooth, for example, 3 separate reference points as shown for reference point 74d.

Periodontal Structures

Acquirable and electronically examinable periodontal structures include, for example, gingival recession or the pulling away of the gums from the teeth, the gingival margin, the free gingival margin, the mucogingival line, minimal attached tissue, furcation, or any combination thereof.

Figure 10:
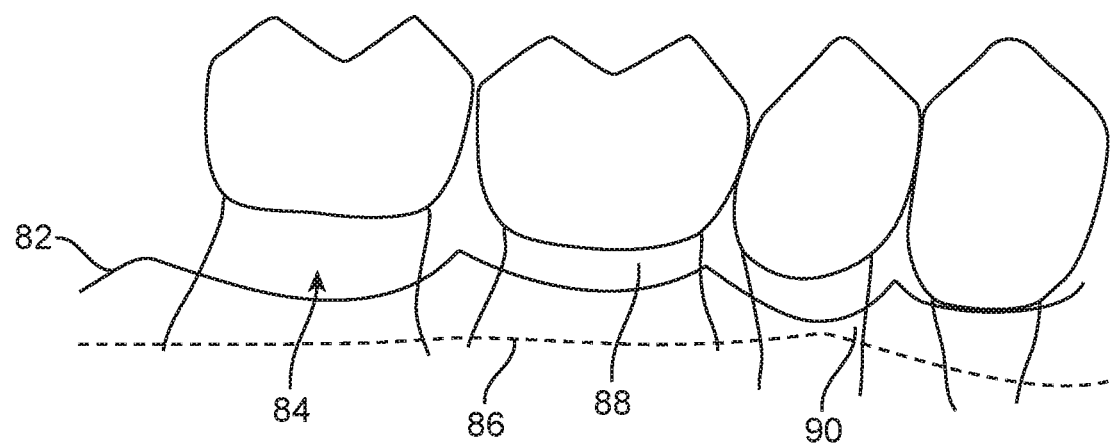
FIG. 10 illustrates a diagrammatic representation of a variation of various periodontal structures including the gingival margin (GM), furcation, mucogingival line (MGL), recession, and minimally attached tissue (MAT).

The gingival margin is the position of the free gingival margin in relation to the cervical enamel junction of the tooth. The free gingival margin is the interface between the sulcular epithelium and the epithelium of the oral cavity. The mucogingival line is the delineation of the attached gingival and the mucosa. Furcations represent a level of recession and bone loss that expose the junction of the root formations of posterior teeth. FIG. 10 illustrates a diagrammatic representation of various periodontal structures including the gingival margin (GM) 82, furcation 84, mucogingival line (MGL) 86, recession 88, and minimally attached tissue (MAT) 90. The size and extent of these features can represent reference points that the system 100 can identify and quantify so that they can each be tracked over time in one or more subsequent data acquisitions after an initial data acquisition.

Although not illustrated in FIGS. 2A-10, the system 100 can mark healthy portions of a dentition with one or more reference points as well, to indicate that one or more portions of a tooth or multiple teeth are currently unaffected by deterioration or deficiency. This can make the emergence of dental conditions, diseases, and/or deficiencies easier to track.

As described above, the data acquisition device 102 can record the structure and extent of these features. The processing unit 104 can "examine" data acquisition data by analyzing it such that the various illustrated and non-illustrated features can be quantified and mapped.

Method of Use

Figure 11:
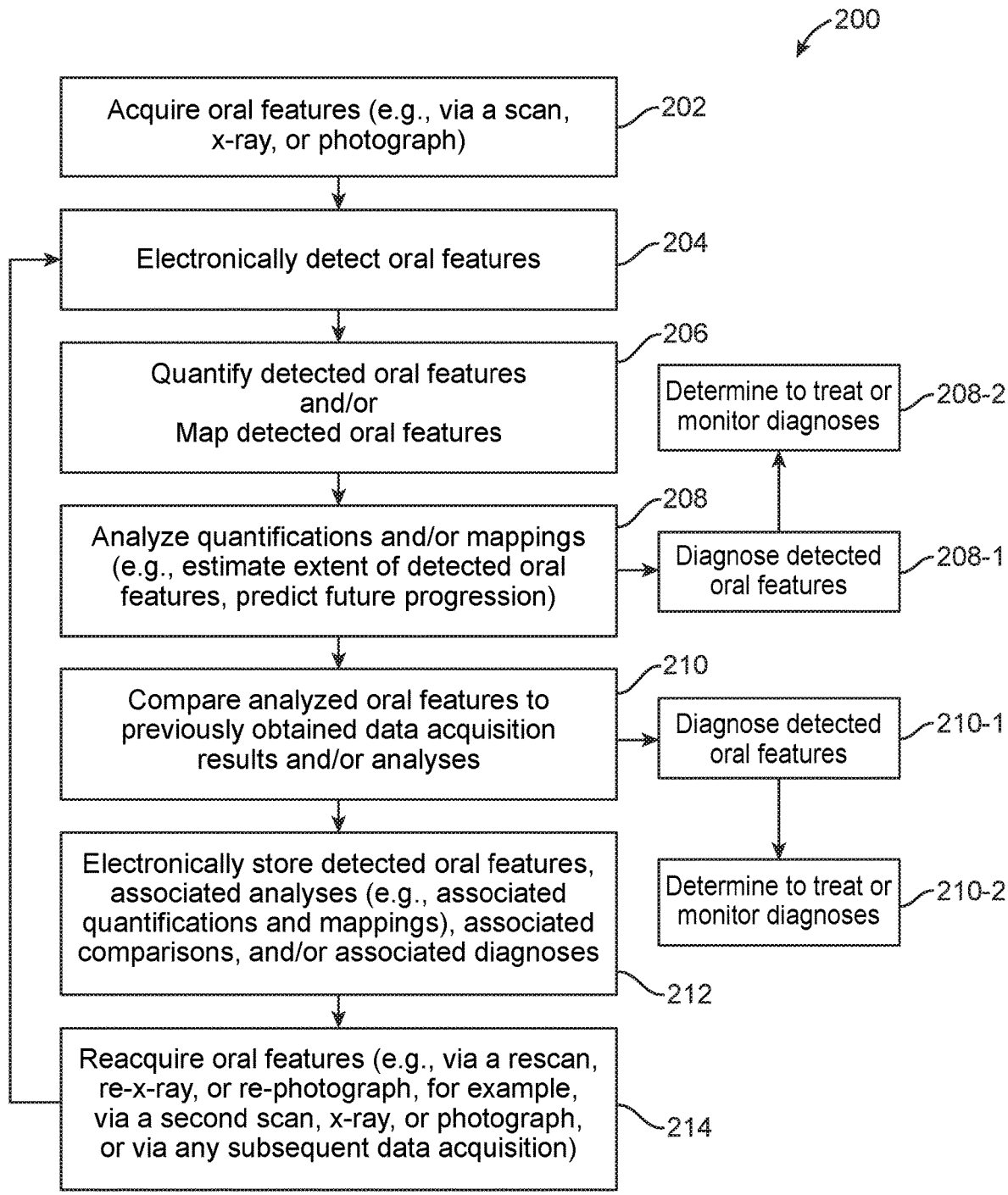
FIG. 11 illustrates a variation of a process undertaken by the system.

FIG. 11 illustrates a variation of a process 200 that is implementable using and/or performable by the system 100. The method 200 can involve acquiring (e.g., detecting and/or observing, for example, scanning, x-raying, photographing) oral features with one or more data acquisition devices 102 in operation 202. The data acquisition in operation 202 can be an initial baseline data acquisition, any subsequent data acquisition (e.g., a data acquisition after the baseline data acquisition or any other data acquisition), or any standalone data acquisition unrelated to any previous or future data acquisition.

The method 200 can further involve electronically detecting one or more oral features in a data acquisition (e.g., one or more images acquired via a scan, an x-ray, a photograph, or any combination thereof) of one or multiple patients (e.g., patient 101) in operation 204. The features can be detected as described herein, for example, by identifying anatomical markers and/or patterns (e.g., peaks, valleys, geometries, shapes, lines, perimeters, outlines, or any combination thereof), the relative positions of soft and/or hard tissues to another soft and/or hard tissue (e.g., the relative positions of one or more anatomical markers to one or more other of the same or different anatomical markers), light absorption, light reflection, colors (e.g., hues), tints, tones, and shades of colors (e.g., light, medium, and/or dark shades of a hue), changes in any of the foregoing, or any combination thereof. The features detected can be one or more reference points, or the reference points can be derived from one or more of the features detected (e.g., from the raw data associated with a data acquisition).

The method 200 can further involve digitally analyzing/assessing the detected features in operation 206, for example, by quantifying (e.g., measuring) and/or mapping the features that are detected with the processing unit 106. Although not shown in FIG. 11, operations 204 and 206 can be reversed such that the hard and/or soft tissues associated with the masticatory system can first be quantified and/or mapped by analyzing the acquired data, after which the oral features can be detected from and/or by analyzing the quantifications and/or mappings. Also not shown in FIG. 11, operation 204 can be omitted altogether such that the oral features can be quantified and/or mapped without any associated (e.g., preceding, concurrent, or subsequent) detection analysis, or can be combined with operation 206 such that the quantification and/or mapping of the acquired data is the detection of oral features, i.e., the features that are quantified and/or mapped are the features detected.

The method 200 can further involve analyzing the quantifications and/or mappings in operation 208. For example, the processing unit 106 can use the quantifications and/or mappings to estimate the extent of the existing conditions, make diagnoses and/or prognoses, determine whether to treat or monitor the existing conditions, determine whether to preventatively treat not yet manifested conditions, recommend one or more treatments and/or treatment regimes, develop educational plans, or any combination thereof, as described in more detail above in relation to the system 100. FIG. 11 illustrates, for example, a diagnosis decision in operation 208-1 and a determination to treat or monitor the diagnoses in operation 208-2.

The method 200 can further involve comparing the acquired data, detected features, and/or analyses (e.g., quantifications, and/or mappings) to previously obtained data acquisitions and/or data acquisition analyses in operation 210. In addition to or in lieu of operations 208-1 and 208-2, FIG. 11 illustrates that these operations can occur in operations 210-1 and 210-2 such that the comparison operation 210 can be, but need not be, informative or otherwise a contributing factor in the diagnose, treatment, and/or monitor determinations in operations 210-1 and 210-2.

The method 200 can further involve electronically storing any of the data associated with and/or derived from the operations described in this disclosure, for example, those shown in method 200, including operations 202, 204, 206, 208, 208-1, 208-2, 210, 210-1, 210-2 (e.g., in data logs or other data representative of stored data), and/or any data and/or analyses associated with a reacquisition of data (e.g., a rescan, a second or subsequent x-ray, a second or subsequent photograph) of oral features in operation 212.

The method 200 can further involve reacquiring (e.g., rescanning, re-x-raying, re-photographing) oral features of a patient (e.g., patient 101) in operation 214 and repeating and performing operations 202, 204, 206, 208, 208-1, 208-2, 210, 210-1, 210-2, 212, 214, or any combination thereof.

The operations 202, 204, 206, 208, 208-1, 208-2, 210, 210-1, 210-2, 212, 214 can be interchangeably combined, rearranged, substituted, and/or omitted in any combination, and can be executed in any order, for example, in the order shown. Additional operations that are not shown can be added to the method 200 or can be part of a separate implementable and/or performable method, for example, making prognoses, predicting the manifestation of not yet manifested conditions, identifying causal variables (e.g., physiological, psychological, bacterial, and/or environmental variables), generating treatment plans, making recommendations regarding treatment and monitoring, or any combination thereof, as well as any other process or operation described or contemplated herein.

Figure 12:
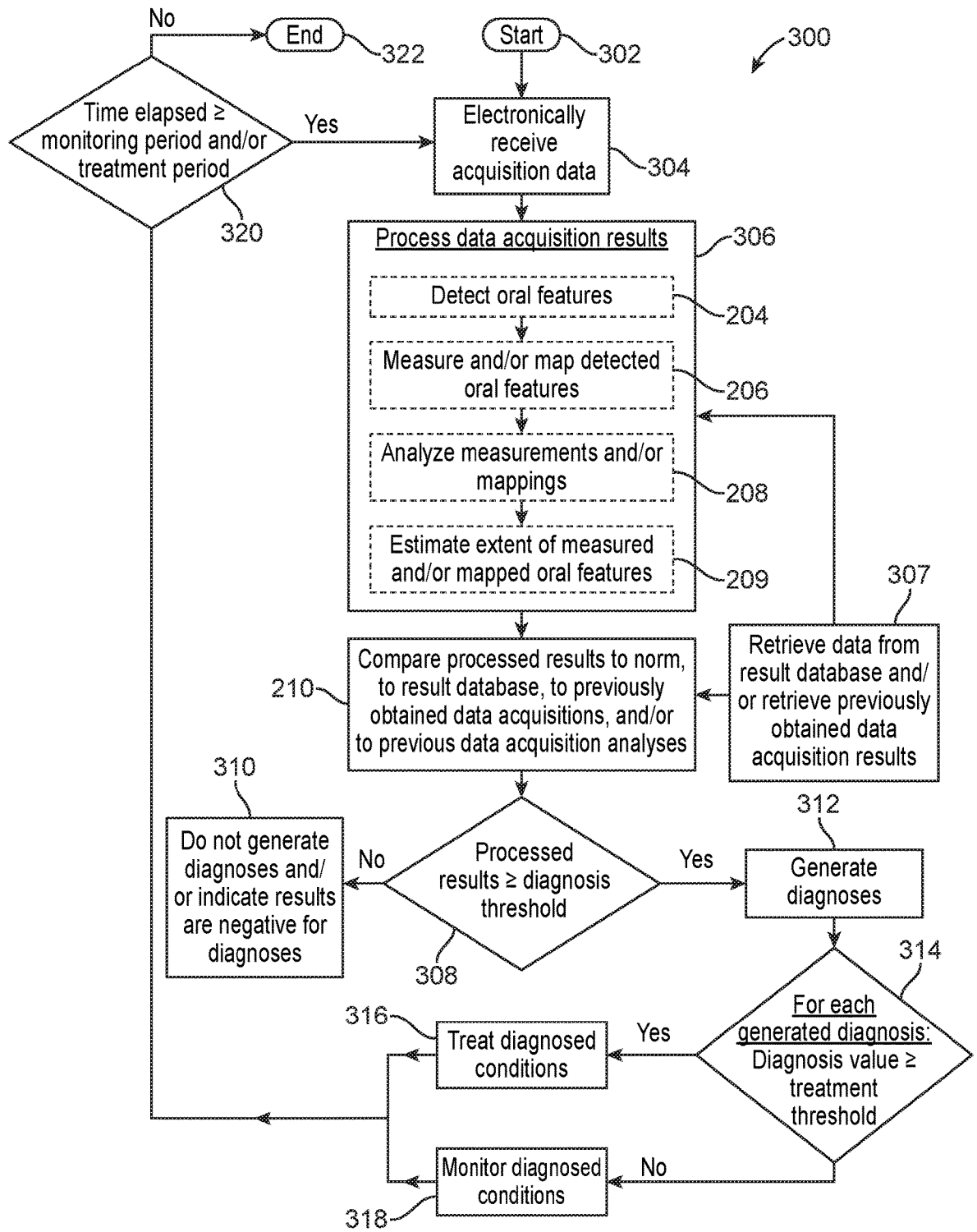
FIG. 12 illustrates a variation of an algorithm executed by the system.

FIG. 12 illustrates a variation of an algorithm 300 executable by the system 100, for example, by the processing unit 106, a cloud server, software spread over a network, or any combination thereof, in addition to any other processing protocol described and contemplated herein. The algorithm 300 can be executable code stored in the memory unit 108 or in an external memory, for example, on a server.

The algorithm 300 can start in operation 302. Upon starting, the algorithm 300 can involve receiving data associated with a data acquisition, for example, data from one or multiple data acquisitions carried out in operation 202. Alternatively, or in combination, the algorithm 300 can start automatically upon receiving acquired data in operation 304.

The algorithm 300 can further involve processing acquired data in operation 306. For example, FIG. 12 illustrates that the processing unit 106 can perform operations 204, 206, 208, or any combination thereof. Features can be detected in operation 204. The detected features can be quantified (e.g., measured) and/or mapped in operation 206. In operation 208 the quantifications and/or mappings can be analyzed. As described above with reference to FIG. 11, operations 204, 206, and 208 can be interchangeably combined, rearranged, substituted, and/or omitted to achieve the exact data processing flow desired; they are each again shown here to illustrate a variation of a process flow that the processing unit of the system 100 can implement or otherwise execute in the form of an exemplary executable algorithm. Operation 209 shows that the extent of the quantified (e.g., measured) and/or mapped features can be estimated, for example, by analyzing the quantifications and mappings and linking or otherwise tying this analysis to the digitally captured (e.g., imaged via a scan, an x-ray, a photo, or any combination thereof) soft and/or hard tissue structures, diseases, and/or deficiencies. For example, operation 209 can be executed if a threshold condition in operation 208 is satisfied, for example, if a ratio of one or more aspects of a tissue or tissue feature satisfies or exceeds a threshold ratio.

The algorithm 300 can further involve performing statistical analysis on the data generated in operation 306 and/or on the raw acquired data received in operation 304. The processing unit 106 can compare the processed results to one or more statistical variables (e.g., qualitative and/or quantitative variables) or any other benchmark value, to previous results, and/or to one or more libraries of data in databases (e.g., corresponding to data from one or multiple people). For example, the data in operation 210 can be compared to statistical values such as norms, averages, maximums, minimums, standard deviations, ratios, or any combination thereof. As shown in FIG. 12, processed and/or raw data can be compared to norms, result databases, and/or to previously obtained data acquisition results (e.g., raw and/or analyzed acquisition data) in operation 210. The algorithm 300 can, for example, further involve retrieving or otherwise referencing data from a result database (e.g., from memory unit 108 and/or external database 112) in operation 307 and/or can involve retrieving or otherwise referencing previously obtained data acquisition results from the same patient and/or one or multiple different patients (e.g., stored in memory unit 108 and/or external database 112) in operation 307. FIG. 12 illustrates that data can be retrieved in operation 307 during any processing step in operation 306, for example, in operation 204, 206, 208, and/or 209. Further, operation 210 can be performed within or part of operation 306 even though operation 210 is illustrated separate from operation 306.

The algorithm 300 can further involve determining whether to generate a diagnosis in operation 308. For example, if a processed result is greater than or equal to a diagnosis threshold, the algorithm 300 can involve generating one or more diagnoses in operation 312. If the processed result is less than the diagnosis threshold, the algorithm 300 can involve not generating a diagnosis and/or indicating that there are currently no existing conditions related to the processed result in operation 310.

The algorithm 300 can further involve determining, for each generated diagnosis (e.g., in operation 312), whether to treat or monitor the condition or conditions associated with each generated diagnosis. For example, if a diagnosis value is greater than or equal to a treatment threshold, the algorithm 300 can involve making a recommendation to treat the diagnosed conditions in operation 316. If the diagnosis value is less than the treatment threshold, the algorithm 300 can involve making a recommendation to monitor the diagnosed conditions in operation 318.

The algorithm 300 can further involve determining whether to make a recommendation to reacquire data (e.g., rescan, re-x-ray, re-photograph) of the patient (e.g., patient 101) in operation 320. For example, operation 320 shows that if an elapsed time is greater than or equal to the monitoring period and/or treatment period, the algorithm 300 can involve making a recommendation to reacquire data of the patient, return to operation 304 and receive the reacquisition data associated with the data reacquisition. If the elapsed time is less than the monitoring period and/or treatment period, the algorithm 300 can end in operation 322 or can involve indicating that it is not yet time to reacquire data of the patient and then end in operation 322. Although not shown in operation 320, the algorithm 300 can make a recommendation of whether to reacquire data of a patient (e.g., patient 101) based on one or more error thresholds or error indicators. Errors can be determined for the acquired data, reacquired data, processed data, and/or analyzed data, including the quantifications and/or mappings thereof. If a calculated or determined error is greater than or equal to a threshold error, the algorithm 300 can involve making a recommendation to reacquire data of the patient, return to operation 304 and receive the acquired data associated with the reacquisition. The data reacquisition can involve a comprehensive acquisition or can involve a focused acquisition that concentrates on the areas or conditions associated with the error. If the calculated or determined error is less than the threshold error, the algorithm 300 can end in operation 322 and/or determine whether an elapsed time is greater than or equal to the monitoring period and/or treatment period as described above.

Figure 13:
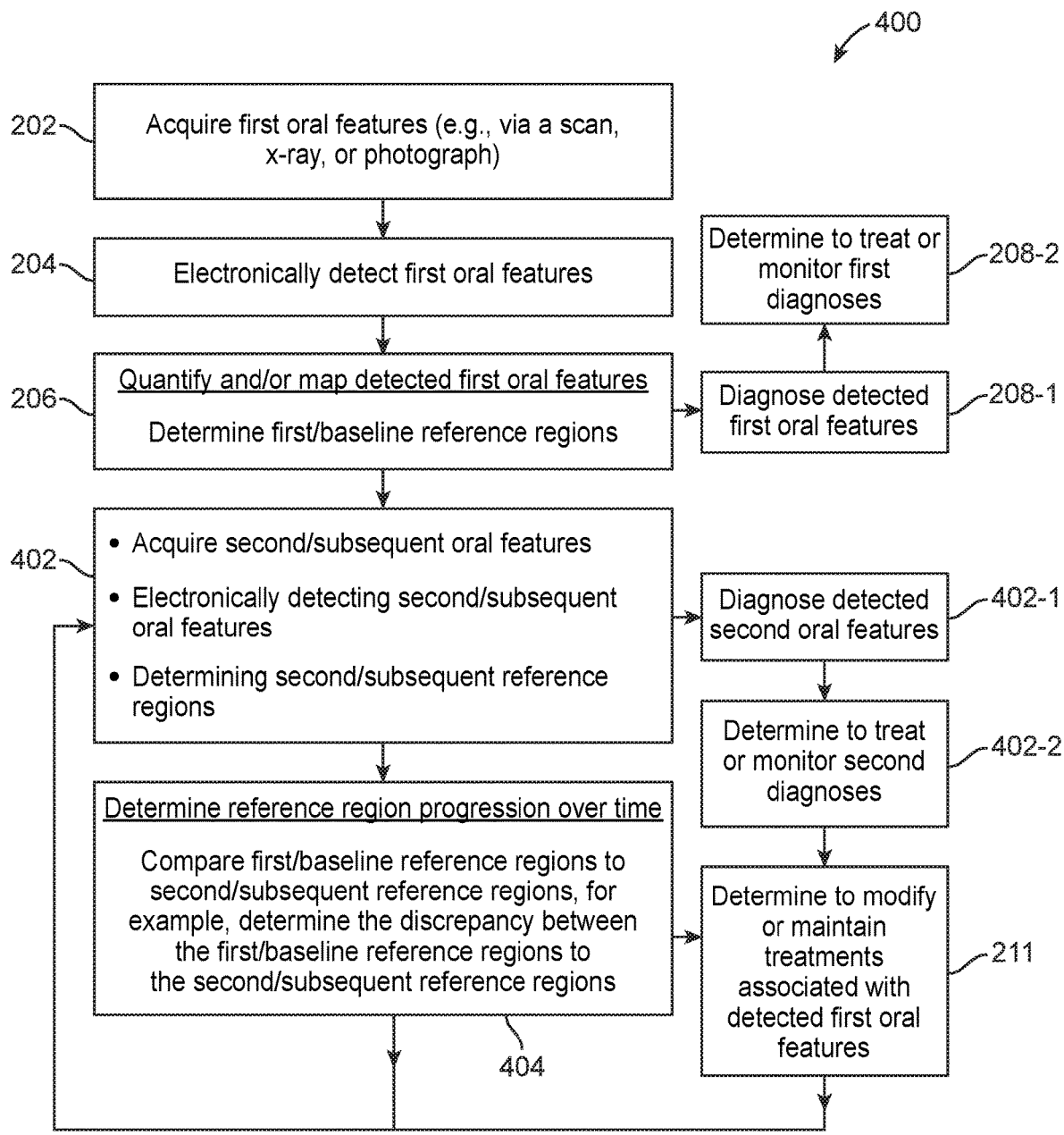
FIG. 13 illustrates a variation of a process undertaken by the system.

FIG. 13 illustrates a variation of a process 400 that is implementable using and/or performable by the system 100. The process 400 can be an algorithm 400 executable by the system 100, for example, by the processing unit 106, a cloud server, software spread over a network, or any combination thereof, in addition to any other processing protocol described and contemplated herein. The algorithm 400 can be executable code stored in the memory unit 108 or in an external memory, for example, on a server.

The method 400 can involve acquiring (e.g., detecting and/or observing, for example, scanning, x-raying, photographing) oral features with one or more data acquisition devices 102 in operation 202. The data acquisition in operation 202 can be an initial baseline data acquisition, any subsequent data acquisition (e.g., a data acquisition after the baseline data acquisition or any other data acquisition), or any standalone data acquisition unrelated to any previous or future data acquisition. For example, FIG. 13 illustrates that operation 202 can involve acquiring one or more first oral features that can correspond to a baseline data acquisition.

The method 400 can further involve electronically detecting one or more oral features in a data acquisition (e.g., one or more images acquired via a scan, an x-ray, a photograph, or any combination thereof) of one or multiple patients (e.g., patient 101) in operation 204 as described above with reference to method 200.

The method 400 can further involve digitally analyzing/assessing the detected features in operation 206, for example, by quantifying (e.g., measuring) and/or mapping the detected first oral features. Although not shown in FIG. 13, operations 204 and 206 can be reversed such that the hard and/or soft tissues associated with the masticatory system can first be quantified and/or mapped by analyzing the acquired data, after which the oral features can be detected from and/or by analyzing the quantifications and/or mappings. Also not shown in FIG. 13, operation 204 can be omitted altogether such that the oral features can be quantified and/or mapped without any associated (e.g., preceding, concurrent, or subsequent) detection analysis, or can be combined with operation 206 such that the quantification and/or mapping of the acquired data is the detection of oral features, i.e., the features that are quantified and/or mapped are the features detected FIG. 13 illustrates that the first oral features can be quantified and/or mapped by determining one or more first (also referred to as baseline) reference regions in operation 206. Each type of dental condition can have one or more reference regions associated with it. For example, FIGS. 2A-10 illustrate variations of various reference regions that the system 100 can identify, quantify, and map. Although not illustrated in operation 206, one or more first (also referred to as baseline) potential reference regions can be determined in operation 206 as well. As described above, the reference regions can be derived from the potential reference regions, or vice versa.

Based on the reference regions quantified and/or mapped in operation 206, the processing unit 106 can estimate the extent of the existing conditions, make diagnoses and/or prognoses, determine whether to treat or monitor the existing conditions (e.g., the conditions detected), determine whether to preventatively treat not yet manifested conditions, recommend one or more treatments and/or treatment regimes, develop educational plans, or any combination thereof, as described in more detail herein in relation to the system 100. FIG. 13 illustrates, for example, that the method 400 can involve diagnosing (or otherwise identifying) the first oral features in operation 208-1, for example, based partly or completely on the reference regions quantified and/or mapped in operation 206, and can involve determining whether to treat or monitor the diagnosed first conditions in operation 208-2.

The method 400 can further involve operation 402, which can involve performing (e.g., repeating, or performing for the first time) operations 202, 204, and/or 206 for one or more second (also referred to as one or more subsequent) oral features. Operation 402 can involve performing operations 202, 204, and/or 206 for the first time where the first oral features were input manually into the system 100, for example, after an in-person review of a dental record, electronic or physical. Although not illustrated in operation 402, one or more second/subsequent potential reference regions can be determined in operation 402 as well. From operation 402, FIG. 13 illustrates that the method 400 can involve diagnosing (or otherwise identifying) the second oral features in operation 402-1, for example, based partly or completely on the reference regions quantified and/or mapped in operation 402, and can involve determining whether to treat or monitor the diagnosed second conditions in operation 402-2.

The method 400 can further involve determining the progression of the reference regions over time in operation 404. For example, operation 404 can involve performing operations 208, 210, and/or 212 as described above with reference to method 200. As shown in FIG. 13, operation 404 can involve comparing one or more first/baseline reference regions to one or more second/subsequent reference regions, for example, by determining the discrepancy (also referred to as a change) between a first/baseline reference region and a second/subsequent reference region. The determined change can be numeric (e.g., difference between two values) and/or graphical in nature (e.g., a darker or lighter color, and/or representation showing improvement or decay, for example, on a graph).

The method 400 can further involve determining whether to modify, maintain, and/or terminate one or more of the treatments associated with one or more of the first conditions in operation 211. The method 400 can further involve whether to add or start one or more new treatments in operation 211. The determinations in operation 211 can be based partly or completely on the comparison between one or more first and second reference regions in operation 404, the second conditions diagnosed in operation 402-1, and/or the second conditions determined to be treated in operation 402-2.

The treatment of a condition can be modified or maintained where the condition as measured by the second data acquisition is worse than that as measured by the first data acquisition. Oral features can be determined to be worse in a second condition than in a first condition where, for example, one or more parameters of the reference region have increased or decreased (e.g., the size, surface area, length, width, height or extent has increased or decreased), a color of the reference region has become darker, a color of the reference region has become lighter, blood perfusion in the reference region has increased, blood perfusion in the reference region has decreased), and/or where the rate of disease or deficiency progression exceeds a threshold rate of change.

The treatment of a condition can be modified or maintained where the condition as measured by the second data acquisition is better than that as measured by the first data acquisition. Oral features can be determined to be better in a second condition than in a first condition where, for example, one or more parameters of the reference region have increased or decreased (e.g., the size, surface area, length, width, height or extent has increased or decreased), a color of the reference region has become darker, a color of the reference region has become lighter, blood perfusion in the reference region has increased, blood perfusion in the reference region has decreased), and/or where the rate of disease or deficiency progression exceeds a threshold rate of change.

New treatments can be initiated, for example, where the second data acquisition in operation 402 yields one or more newly detected dental conditions. New dental conditions can be detected in operation 402 where, for example, the conditions had not yet manifested, or were otherwise yet undetectable, in operations 202, 204, and/or 206.

The method 400 can further involve electronically storing any of the data associated with and/or derived from the operations described in this disclosure, for example, those shown and referred to in relation to method 400, including operations 202, 204, 206, 208, 208-1, 208-2, 210, 211, 402, 402-1, 402-2, 404 (e.g., in data logs or other data representative of stored data), and/or any data and/or analyses associated with a reacquisition of data (e.g., a rescan, a second or subsequent x-ray, a second or subsequent photograph).

The method 400 can further involve reacquiring (e.g., rescanning, re-x-raying, re-photographing) oral features of a patient (e.g., patient 101) and repeating and performing the operations shown and referred to in relation to method 400, including operations 202, 204, 206, 208, 208-1, 208-2, 210, 211, 402, 402-1, 402-2, 404, or any combination thereof. For example, arrows 406 in FIG. 13 illustrate that the method 400 can flow from operations 211 and/or 404 to operation 402.

The operations shown and referred to in relation to method 400 can be interchangeably combined, rearranged, substituted, and/or omitted in any combination, and can be executed in any order, for example, in the order shown. Additional operations that are not shown can be added to the method 400 or can be part of a separate implementable and/or performable method, for example, making prognoses, predicting the manifestation of not yet manifested conditions, identifying causal variables (e.g., physiological, psychological, bacterial, and/or environmental variables), generating treatment plans, making recommendations regarding treatment and monitoring, or any combination thereof, as well as any other process or operation described or contemplated herein.

Figure 14:
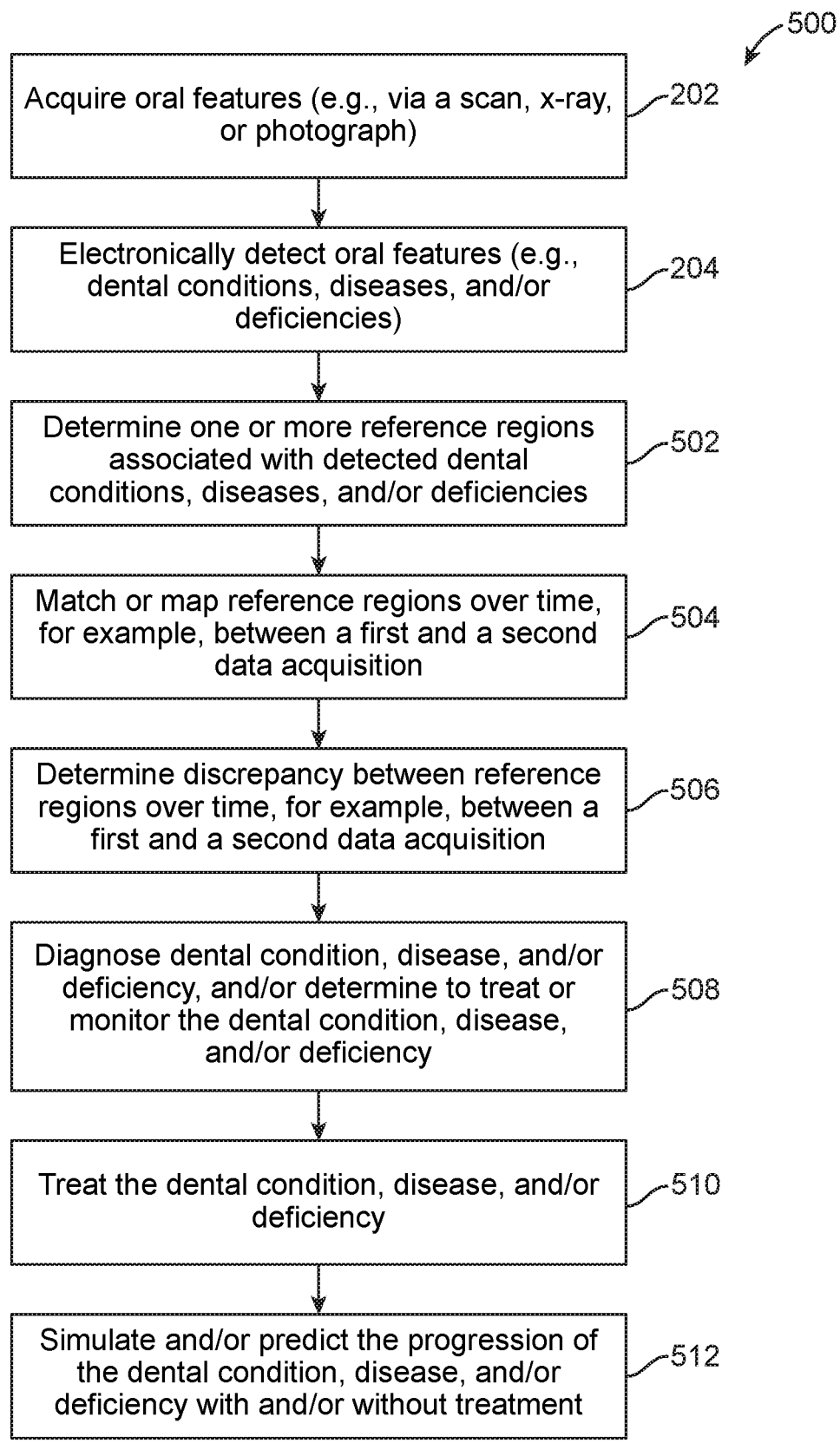
FIG. 14 illustrates a variation of an algorithm executed by the system.

FIG. 14 illustrates a variation of an algorithm 500 that the system 100 can implement to observe, detect, analyze, and electronically document dental conditions, diseases and deficiencies, for example, the dental conditions, diseases and deficiencies shown and described with reference to FIGS. 2A-10.

The algorithm 500 can be executable by the system 100, for example, by the processing unit 106, a cloud server, software spread over a network, or any combination thereof, in addition to any other processing protocol described and contemplated herein. The algorithm 500 can be executable code stored in the memory unit 108 or in an external memory, for example, on a server.

The algorithm 500 can involve operations 202 and 204 as described above, for example, with reference to the methods and algorithms illustrated in FIGS. 11-13.

The algorithm 500 can further involve determining one or more reference points/regions associated with one or more detected oral features in operation 502, for example, one or more detected dental conditions, diseases, and/or deficiencies. Although not illustrated in operation 502, one or more potential reference regions can be determined in operation 502 as well. As described above, the reference regions can be derived from the potential reference regions, or vice versa. For example, the reference and potential reference regions can correspond to those described above (e.g., the reference and potential reference points illustrated in FIGS. 2A-10).

The algorithm 500 can further involve matching or mapping reference regions over time in operation 504, for example, between a first data acquisition and a second or any subsequent data acquisition (i.e., between any two data acquisitions). In this way, the system 100 can track the progression (e.g., improvement, deterioration, or no change) and/or the emergence of dental conditions, diseases, and/or deficiencies over time.

The algorithm 500 can further involve determining a discrepancy (e.g., numerically and/or graphically) between reference regions over time in operation 506, for example, between a first data acquisition and a second or any subsequent data acquisition (i.e., between any two data acquisitions). In this way, the system 100 can track the progression (e.g., improvement, deterioration, or no change) and/or the emergence of dental conditions, diseases, and/or deficiencies over time. For example, improvement of an oral feature can correspond to a positive or negative discrepancy (e.g., an increase or decrease in a value associated with the reference regions between two data acquisitions). Deterioration of an oral feature can correspond to a positive or negative discrepancy (e.g., an increase or decrease in a value associated with the reference regions between two data acquisitions). No change in an oral feature can correspond to zero discrepancy, or an approximately zero discrepancy (e.g., no change in a value associated with the reference regions between two data acquisitions).

From operation 506, FIG. 14 illustrates that the algorithm 500 can involve diagnosing (or otherwise identifying) the dental conditions, diseases, and/or deficiencies in operation 508, for example, based partly or completely on the data determined in operations 502, 504, and 506, and can involve determining whether to treat or monitor the diagnosed dental conditions, diseases, and/or deficiencies in operation 508.

The algorithm 500 can further involve determining treating the dental conditions, diseases, and/or deficiencies in operation 510. Treatment can involve using sealant, one or patches, crowns, and/or veneers. The treatment used can minimize further deterioration, for example, further wear, further erosion, further abrasion, further abfraction, or any other deterioration of the conditions shown and described herein, for example, those shown and described with reference to FIGS. 2A-10. The treatment can recover the original or bring the teeth closer to their original shape. The treatment can treat the dental conditions, diseases, and/or deficiencies such that the original condition of the teeth is not repaired, recovered, or otherwise achieved. The treatments applied to one or more teeth can be designed to make the bit more ideal. For example, for wear, a temporary cap with a hole can be placed over a tooth such that the cap and hole are placed over a reference region indicating wear. Once placed on a tooth, sealant can be injected through the hole such that the cap provides a mold for the sealant when the sealant hardens. The hole can have a one-way valve to prevent sealant from discharging from the cap. The temporary cap can be filled with sealant near the hole prior to placement on the tooth adjacent to the wear. The hole can have a one-way valve that allows sealant to exit the space between the cap and the tooth. During placement, excess sealant can be forced out of the hole and one way valve such that the sealant that remains in the cap can harden according to the shape of the cap. In this way, wear (e.g., the wear in FIG. 2E) can be treated, for example, by first constructing the cap having the hole, introducing sealant to the wear location, and hardening the sealant (e.g., with ultrasound).

The algorithm 500 can further involve simulating and/or predicting the progression of the dental conditions, diseases, and/or deficiencies in operation 512, with and/or without treatment.

A number of variations have been described. Nevertheless, it will be understood by one of ordinary skill in the art that various modifications may be made without departing from the spirit and scope of the variations. In addition, the flowcharts, logic flows, and algorithms depicted in the figures do not require the particular order shown, or sequential order, to achieve desirable results, and are exemplary only. In addition, other steps or operations may be provided, or steps or operations may be eliminated, from the described flows and algorithms, and other components and/or features may be added to, or removed from, the described and contemplated systems. Accordingly, other variations are within the scope of the following claims.

It will be understood by one of ordinary skill in the art that the various methods and processes disclosed herein may be embodied in a non-transitory readable medium, machine-readable medium, and/or a machine accessible medium comprising instructions compatible, readable, and/or executable by a processor or processing unit of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

The claims are not limited to the exemplary variations shown in the figures, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, methods, and algorithms described herein can be used for medical (e.g., diagnostic, therapeutic or rehabilitative) or non-medical purposes.

What is claimed is:

1. A method of electronically diagnosing and tracking the progression of one or more dental conditions, the method comprising:
   determining an oral feature result by processing data of an oral feature;
   diagnosing a dental condition of the oral feature based on the oral feature result;
   tracking the progression of the dental condition over time; and
   simulating at least one of a treatment of the dental condition and the progression of the dental condition.

2. The method of claim 1, wherein processing data of an oral feature comprises at least one of mapping the oral feature and measuring the oral feature.

3. The method of claim 1, wherein processing data of an oral feature comprises at least one of mapping the oral feature, wherein the mapping is at least one of a current mapping of the oral feature and a predictive mapping of the oral feature.

4. The method of claim 1, wherein processing data of an oral feature comprises detecting at least one of a dimension, a contact surface, a shape, a color, a shade, and a measurement of the oral feature.

5. The method of claim 1, wherein the oral feature result comprises an anatomical marker of the dental condition.

6. The method of claim 1, wherein tracking the progression of the dental condition over time comprises determining a discrepancy between the oral feature at a first time and the oral feature at a second time.

7. The method of claim 1, wherein diagnosing a dental condition of the oral feature comprises at least one of comparing the oral feature result to a database of one or more stored oral feature results and comparing the oral feature result to a diagnosis threshold.

8. A method of electronically diagnosing and tracking the progression of one or more dental conditions, the method comprising:
   determining an oral feature result by processing data of an oral feature;
   diagnosing a dental condition of the oral feature based on the oral feature result;
   tracking the progression of the dental condition over time; and
   simulating at least one of the progression of the dental condition with treatment of the dental condition and the progression of the dental condition without treatment of the dental condition.

9. The method of claim 8, wherein processing data of an oral feature comprises at least one of mapping the oral feature, wherein the mapping is at least one of a current mapping of the oral feature and a predictive mapping of the oral feature.

10. A method of electronically diagnosing and tracking the progression of one or more dental conditions, the method comprising:
    diagnosing, via a processor, a dental condition based on data of an oral feature;
    tracking the progression of the dental condition by determining a discrepancy between the oral feature at a first time and the oral feature at a second time; and
    simulating at least one of the progression of the dental condition with treatment of the dental condition and the progression of the dental condition without treatment of the dental condition.

11. The method of claim 10, wherein diagnosing, via a processor, a dental condition comprises diagnosing the dental condition based on a diagnosis threshold.

12. The method of claim 10, further comprising comparing a diagnosis value associated with the dental condition to a treatment threshold.

13. The method of claim 12, further comprising making a determination to treat the dental condition if the diagnosis value exceeds the treatment threshold.

14. The method of claim 13, further comprising simulating a treatment of the dental condition.

15. The method of claim 10, further comprising simulating treatment of the dental condition.

16. A method of electronically diagnosing and tracking the progression of one or more dental conditions, the method comprising:
    diagnosing, via a processor, a dental condition based on data of an oral feature;
    tracking the progression of the dental condition by determining a discrepancy between the oral feature at a first time and the oral feature at a second time; and
    simulating a treatment of the dental condition.

17. The method of claim 16, wherein diagnosing, via a processor, a dental condition comprises diagnosing the dental condition based on a diagnosis threshold.

18. The method of claim 16, further comprising comparing a diagnosis value associated with the dental condition to a treatment threshold.

19. The method of claim 18, further comprising making a determination to treat the dental condition if the diagnosis value exceeds the treatment threshold.

20. The method of claim 16, further comprising simulating at least one of the progression of the dental condition with the treatment of the dental condition and the progression of the dental condition without the treatment of the dental condition.

* * * * *